US012234502B2

(12) United States Patent
Chen et al.

(10) Patent No.: US 12,234,502 B2
(45) Date of Patent: Feb. 25, 2025

(54) OLIGONUCLEOTIDE ASSEMBLY USING PH BASED ELECTRODE CONTROLLED HYBRIDIZATION

(71) Applicant: MICROSOFT TECHNOLOGY LICENSING, LLC, Redmond, WA (US)

(72) Inventors: Yuan-Jyue Chen, Seattle, WA (US); Bichlien Hoang Nguyen, Seattle, WA (US); Karin Strauss, Seattle, WA (US); Jake Allen Smith, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 368 days.

(21) Appl. No.: 17/338,012

(22) Filed: Jun. 3, 2021

(65) Prior Publication Data

US 2022/0389483 A1    Dec. 8, 2022

(51) Int. Cl.
*C12Q 1/6809* (2018.01)
*C12Q 1/6837* (2018.01)
*G01N 15/1433* (2024.01)

(52) U.S. Cl.
CPC ......... *C12Q 1/6809* (2013.01); *C12Q 1/6837* (2013.01); *G01N 15/1433* (2024.01)

(58) Field of Classification Search
CPC .. C12Q 1/6809; C12Q 1/6837; C12Q 1/6823; C12Q 1/6834; C12Q 1/6806; C12Q 2523/307; C12Q 2527/119; G01N 15/1433
See application file for complete search history.

(56) References Cited

U.S. PATENT DOCUMENTS

| | | | |
|---|---|---|---|
| 11,873,484 B2 * | 1/2024 | Chen | G11C 13/02 |
| 2001/0024788 A1 * | 9/2001 | Hashimoto | B01J 19/0046 435/6.12 |
| 2005/0176035 A1 * | 8/2005 | Crothers | C12Q 1/6837 435/6.12 |
| 2007/0037169 A1 * | 2/2007 | Cooper, Jr. | C12Q 1/6837 435/6.12 |
| 2008/0044821 A1 * | 2/2008 | Zainiev | C12Q 1/6837 536/24.3 |
| 2018/0127816 A1 * | 5/2018 | Teo | C12Q 1/6855 |
| 2018/0137418 A1 * | 5/2018 | Roquet | G11C 13/0019 |
| 2019/0244109 A1 * | 8/2019 | Bramlett | G11C 13/0019 |
| 2020/0199662 A1 | 6/2020 | Strauss et al. | |
| 2020/0384434 A1 | 12/2020 | Nguyen et al. | |
| 2021/0155923 A1 | 5/2021 | Chen et al. | |

FOREIGN PATENT DOCUMENTS

| | | |
|---|---|---|
| CN | 109830263 A | 5/2019 |
| WO | 9601836 A1 | 1/1996 |
| WO | 2018102064 A1 | 6/2018 |

OTHER PUBLICATIONS

Song (Nature Communications (2018) vol. 9, pp. 1-8).*
Gamella (Electroanalysis 2017, 29, 398-408).*
Lopez ( Nature Communications | (2019) 10:2933 ).*
Hughes (ColdSpringHarbPerspectBiol2017;9:a023812).*
Li (Molecules 2016, 21, 1393).*
Day (Bioorganic & Medicinal Chemistry 22 (2014) 4407-4418).*
Rahman (Nanoscale Research Letters (2017) 12:484).*
Wong (Nano letters (2009) vol. 9, pp. 3521-3526).*
Organick, et al., "Random Access in Large-Scale DNA Data Storage", In Journal of Nature biotechnology, vol. 36, Issue 3, Mar. 1, 2018, pp. 242-248.
West, Ryanm., "Review—Electrical Manipulation of DNA Self-Assembled Monolayers: Electrochemical Melting of Surface-Bound DNA", In Journal of The Electrochemical Society, vol. 167, Jan. 21, 2020, 9 Pages.
Adam, et al., "Electrochemical Monitoring of the Reversible Folding of Surface-Immobilized DNA i-Motifs", In Journal of Langmuir, vol. 34, Issue 9, Feb. 26, 2018, pp. 3112-3118.
Bi, et al., "Building Addressable Libraries: The Use of "Safety-Catch" Linkers on Microelectrode Arrays", In Journal of the American Chemical Society, vol. 132, Issue 49, Nov. 19, 2010, pp. 17405-17407.
Egeland, et al., "Electrochemically Directed Synthesis of Oligonucleotides for DNA Microarray Fabrication", In Journal of Nucleic Acids Research, vol. 33, Issue 14, Aug. 5, 2005, 7 Pages.
El-Sagheer, et al., "Click Nucleic Acid Ligation: Applications in Biology and Nanotechnology", In Journal of Accounts of Chemical Research, vol. 45, Issue 8, Mar. 22, 2012, pp. 1258-1267.
Ghindilis, et al., "CombiMatrix Oligonucleotide Arrays: Genotyping and Gene Expression Assays Employing Electrochemical Detection", In Journal of Biosensors & Bioelectronics, vol. 22, Issue 9-10, Apr. 15, 2007, pp. 1853-1860.

(Continued)

*Primary Examiner* — Narayan K Bhat
(74) *Attorney, Agent, or Firm* — Benjamin A. Keim; Newport IP, LLC

(57) ABSTRACT

Electrode controlled hybridization is used to change local pH and selectively assemble oligonucleotide complexes on the surface of a microelectrode array. The oligonucleotide complexes have sticky ends that provide locations for subsequent oligonucleotide complexes to hybridize. The order in which specific oligonucleotide complexes are joined together encodes information. Controlled activation of individual electrodes in the microelectrode array creates negative voltages that reduces a buffer solution and raises the pH in proximity to the electrodes. At higher pH levels double-stranded oligonucleotides de-hybridize. Nicks between oligonucleotide complexes and oligonucleotides anchored to the microelectrode array are closed creating covalent attachments. De-hybridized single-stranded oligonucleotides are removed leaving only the oligonucleotides connected to microelectrode array. Thus, during a given round of synthesis, oligonucleotide complexes are added only to the locations on the microelectrode array where the electrodes are not activated.

20 Claims, 12 Drawing Sheets

(56) References Cited

OTHER PUBLICATIONS

Hoff, et al., "Rapid and Dynamic Nucleic Acid Hybridization Enables Enzymatic Oligonucleotide Synthesis by Cyclic Reversible Termination: A Novel Mechanism for Enzymatic DNA Synthesis", In Repository of bioRxiv, Apr. 15, 2019, 23 Pages.

Hughes, et al., "Synthetic DNA Synthesis and Assembly: Putting the Synthetic in Synthetic Biology", In Journal of Cold Spring Harbor Perspectives in Biology, vol. 9, Issue 1, Jan. 1, 2017, 18 Pages.

Lopez, et al., "DNA Assembly for Nanopore Data Storage Readout", In Journal of Nature Communication, vol. 10, Issue 1, Jul. 3, 2019, 9 Pages.

Ma, et al., "Single-Stranded DNA Cleavage by Divergent CRISPR-Cas9 Enzymes", In Journal of Molecular Cell, vol. 60, Issue 3, Nov. 5, 2015, pp. 398-407.

Maurer, et al., "Electrochemically Generated Acid and Its Containment to 100 Micron Reaction Areas for the Production of DNA Microarrays", In Journal of PLos One, vol. 1, Issue 1, Dec. 20, 2006, 7 Pages.

"International Search Report and Written Opinion Issued in PCT Application No. PCT/US20/059761", Mailed Date: Feb. 17, 2021, 15 Pages.

Song, et al., "DNA Multi-Bit Non-Volatile Memory and Bit-shifting Operations using Addressable Electrode Arrays and Electric Field-Induced Hybridization", In Journal of Nature Communications, vol. 9, Article No. 281, Jan. 18, 2018, 8 Pages.

Takahashi, et al., "Demonstration of End-to-End Automation of DNA Data Storage", In Journal of Scientific Reports, vol. 09, Issue No. 1, Mar. 21, 2019, 5 Pages.

"Notice of Allowance Issued in U.S. Appl. No. 16/698,860", Mailed Date: Sep. 7, 2023, 7 Pages.

"Non Final Office Action Issued in U.S. Appl. No. 16/698,860", Mailed Date: Jan. 30, 2023, 8 Pages.

"International Search Report and Written Opinion Issued in PCT Application No. PCT/US22/028408", Mailed Date: Aug. 12, 2022, 12 Pages.

"Notice of Allowance Issued in European Patent Application No. 20817573.7", Mailed Date: Jul. 18, 2023, 8 Pages.

"Final Office Action Issued in U.S. Appl. No. 16/698,860", Mailed Date: Jun. 26, 2023, 15 Pages.

Edman, et al., "Electric Field Directed Nucleic Acid Hybridization on Microchips", In Journal of Nucleic Acids Research, vol. 25, Issue 24, Dec. 1, 1997, pp. 4907-4914.

\* cited by examiner

BEFORE APPLYING NEGATIVE VOLTAGE

AFTER APPLYING NEGATIVE VOLTAGE

OLIGONUCLEOTIDE ASSEMBLY USING PH BASED ELECTRODE CONTROLLED HYBRIDIZATION

BIOLOGICAL SEQUENCES

Although this application references nucleotide sequences and uses single-letter abbreviations to represent individual nucleic acid bases, it does not include any nucleotide sequences as defined in 37 C.F.R. 1.821 because there are no sequences of ten or more nucleotides.

BACKGROUND

Synthetic DNA is an attractive medium for long-term data storage due to its density, ease of copying, sustainability, and longevity. The most challenging hurdle in deployment of a DNA data storage system remains writing data to DNA by synthesizing oligonucleotides. The vast majority of artificially synthesized oligonucleotides are created by chemical synthesis using the phosphoramidite process. This process involves multiple steps and is performed using the organic solvent acetonitrile. Oligonucleotides may also be synthesized enzymatically using a template-independent DNA polymerase such as terminal deoxynucleotidyl transferase (TdT).

However, both techniques have drawbacks. The phosphoramidite process is complex and creates organic waste that can be hazardous and expensive to process. Additionally, the phosphoramidite process uses phosphoramidites which are nucleotides modified with protecting groups. Phosphoramidites are expensive and may create artifacts in some applications due to the modifications.

Enzymatic synthesis addresses some of the deficiencies of the phosphoramidite process. However, the TdT enzyme adds nucleotides in an unregulated manner. Unless controlled, enzymatic synthesis creates unintended homopolymers by repeatedly adding the same nucleotide multiple times. Multiple techniques have been identified to limit homopolymer creation but each increases complexity and comes with its own set of drawbacks.

Alternative ways of writing arbitrary data to oligonucleotides that avoid the limitations of current chemical and enzymatic synthesis techniques may find use in multiple applications such as DNA data storage and gene assembly. The following disclosure is made with respect to these and other considerations.

SUMMARY

This disclosure provides methods and devices for writing digital information by assembling small "oligonucleotide complexes" into long oligonucleotides with the assist of pH based electrode-controlled hybridization on a microelectrode array. Switching on electrodes to negative voltages can generate a sufficiently basic local environment to prevent oligonucleotide hybridization. As such, the oligonucleotide complexes can be controlled to assemble on only switched-off electrodes. This enables controlled writing of information-encoding oligonucleotides in a paralleled manner.

Oligonucleotide complexes are flowed into a reaction chamber in contact with the microelectrode array. The microelectrode array is coated with a plurality of anchor strands to which the oligonucleotide complexes hybridize forming partially double-stranded structures. These double-stranded structures are separated into two single-stranded oligonucleotides where electrodes are activated with a negative voltage. The negative voltage reduces water molecules in proximity to the electrodes raising the pH and creating a localized basic environment. The environment is sufficiently basic (e.g., above about pH 9) such that double-stranded oligonucleotides de-hybridize. Loss of double-stranded structure causes the oligonucleotide complexes to disassociate from the surface of the microelectrode array. The oligonucleotides that are not hybridized to or covalently attached to the anchor strands may then be washed away.

The remaining double-stranded oligonucleotides are covalently attached to the anchor strands by closing nicks such as through ligation or by creating an alternative backbone using a click chemistry reaction. This process is repeated thereby adding additional oligonucleotide complexes onto the ends of oligonucleotide complexes already attached to the microelectrode array. Thus, during each round of extension, the growing oligonucleotides are extended at the locations where electrodes are not activated with a negative voltage.

The oligonucleotides in solution are "oligonucleotide complexes" that include a pre-synthesized payload region encoding arbitrary information or carrying a portion of a gene. Oligonucleotide complexes have a double-stranded (ds) payload region flanked by two single-stranded (ss) sticky ends or overhangs. The payload region may encode any arbitrary value such as a bit ("0" or "1"), a character (A, B, C, D, . . . ), or any other value. The payload region may also encode a sequence that has biological meaning such as all or part of a gene.

The oligonucleotide complexes have two sticky ends. Thus, the oligonucleotide complexes may hybridize to single-stranded oligonucleotides with a sequence that is complementary to either of the two sticky ends. One of the sticky ends may hybridize to anchor sequences attached to the surface of the microelectrode array. The other sticky end provides a single-stranded region for a subsequent oligonucleotide complex to hybridize. Oligonucleotide complexes may be added sequentially, each hybridizing to the sticky end created by the previous one. The oligonucleotide sequences anchored to the microelectrode array, anchor sequences, and the oligonucleotide sequences in solution are designed so that they are at least partially complementary.

The oligonucleotide complexes are incubated with the microelectrode array under suitable conditions and for sufficient time such that they hybridized to complementary sequences attached to the surface of the microelectrode array. Different combinations of electrodes may be activated at each round of assembly creating locations where the oligonucleotide complexes cannot hybridize. Spatial control of oligonucleotide complex addition at the level of individual microelectrodes provides a high degree of parallelism and enables creation of a large number of oligonucleotides with unique sequences.

In an alternative implementation, i-motif sequences that change from a folded confirmation at low pH to an unfolded confirmation at neutral or high pH are used to regulate attachment of oligonucleotide complexes. An i-motif sequence is an oligonucleotide sequence that includes multiple cytosine triplets. The i-motif sequences may be used as anchor sequences attached to the surface of the microelectrode array or as a sticky end on an oligonucleotide complex. Selective activation of microelectrodes to generate positive voltages creates localized acidic environments which change the i-motif sequences into folded confirmations that are not available for hybridization. Thus, oligonucleotide complexes would not be able to hybridize and extend growing oligonucleotides at locations where electrodes are activated.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The figures are schematic representations and items shown in the figures are not necessarily to scale.

DETAILED DESCRIPTION

Figure 1A:
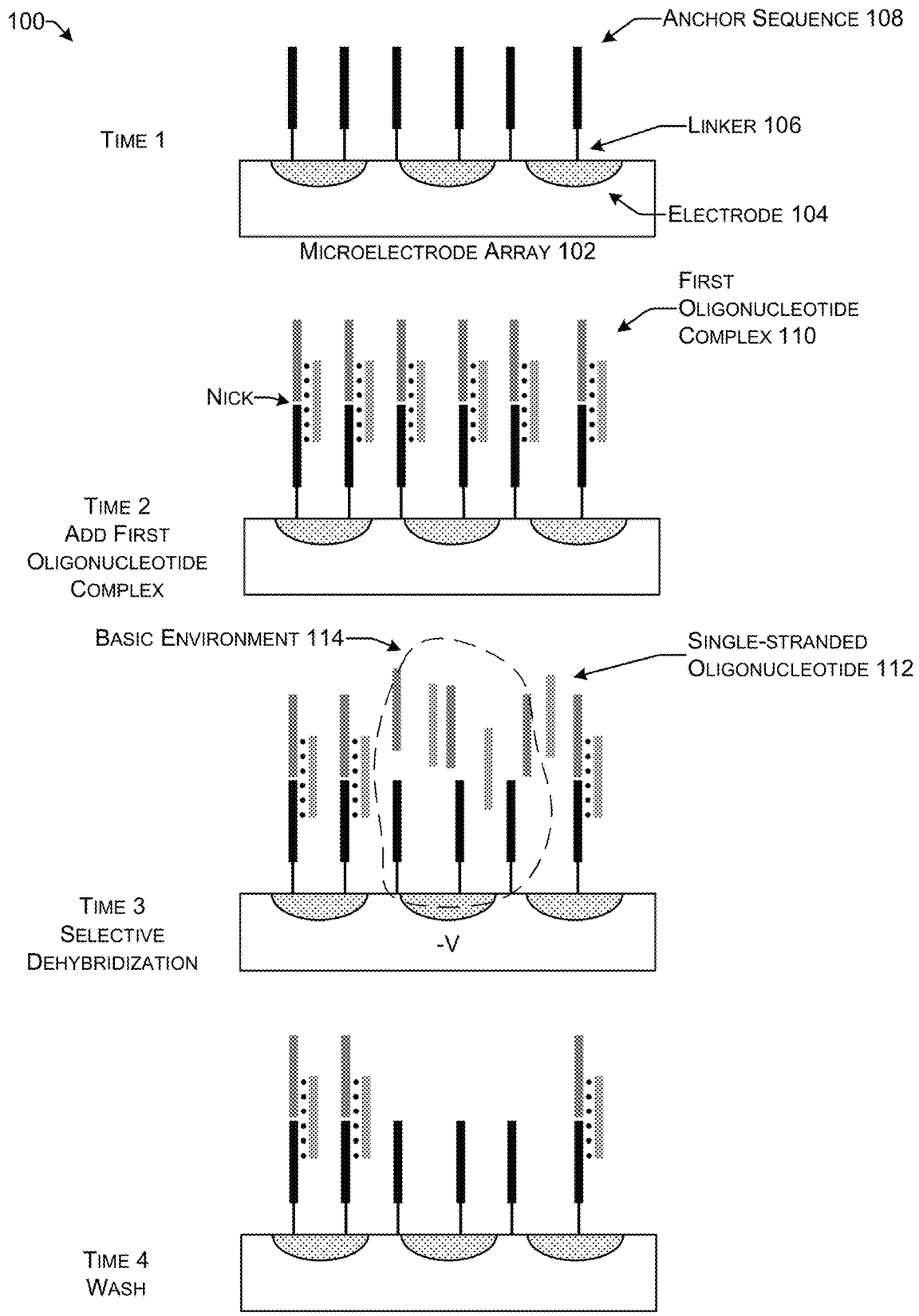
FIGS. 1A-C illustrates creation of oligonucleotides by combining multiple oligonucleotide complexes at locations controlled by selective activation of individual electrodes on a microelectrode array.

This disclosure provides techniques that use electrically controlled hybridization to selectively assemble oligonucleotides with specific, arbitrary sequences. These assembly techniques are alternatives to conventional phosphoramidite oligonucleotide synthesis and enzymatic oligonucleotide synthesis. The assembly techniques presented in this disclosure are performed in aqueous solution with common reagents. These techniques are readily adapted for automated or semiautomated systems such as microfluidic or laboratory robotics systems and may be used for massively parallel creation of oligonucleotides without generation of organic solvent waste as in the phosphoramidite method or introduction of undesired homopolymers as with enzymatic synthesis.

Electrically controlled hybridization uses electrodes on a microelectrode array to create localized pH changes that cause double-stranded oligonucleotides to de-hybridize. Negative charges created at one or more microelectrodes reduce a buffer solution leading to a basic environment with a pH of about 9 or higher. This causes oligonucleotide complexes to de-hybridize and single-stranded oligonucleotides that are not attached to the surface of the microelectrode array can be washed away. This creates site-selectivity, causing oligonucleotide extension only at those electrodes that are not activated with a negative voltage.

Above pH 9, standard duplexes are destabilized because of titration of the polar groups on the bases. Polar groups are involved in hydrogen bonding between base pairs. Ionization adds a net charge to polar bonds. High pH, up to 13, is less damaging and is used to denature nucleic acids. At pH 9 or higher, DNA is susceptible to alkaline denaturation due to the abundance of hydroxide ions. These negatively-charged ions remove hydrogen ions from the base pairs of DNA, thereby breaking the hydrogen bonds between and causing the DNA strands to denature. Roberts R W, Crothers D M. *Stability and properties of double and triple helices: dramatic effects of RNA or DNA backbone composition.* Science. 258:1463-6 (1992).

The microelectrode array is coated with anchor oligonucleotides that are single-stranded oligonucleotides attached to the surface of the microelectrode array through functionalization or by a linker. Many linkers and other techniques for attaching oligonucleotide strands to the surface of a substrate are known to those of ordinary skill in the art. Examples include silane functionalization which covers a surface with organofunctional alkoxysilane molecules. Examples of linkers that may be used are provided in U.S. Pat. Pub. No. US 2020/0199662 A1 filed on Dec. 21, 2018, with the title "Selectively Controllable Cleavable Linkers." Non-covalent attachment such as streptavidin-biotin interactions may also be used to attach the anchor oligonucleotides to the microelectrode array.

The microelectrode array may contain a large number of microelectrodes that make it possible to create many different oligonucleotides (e.g., 10,000, 60,000, 90,000, or more) on the surface of a single array. This high level of multiplexing is made possible in part by the microelectrode density which may be approximately 1000 microelectrodes/$cm^2$, 10,000 microelectrodes/$cm^2$, or a different density. Examples of suitable microelectrode arrays are provided in Bo Bi et al., *Building Addressable Libraries: The Use of "Safety-Catch" Linkers on Microelectrode Arrays,* 132 J. Am. Chem. Soc. 17,405 (2010) and in U.S. Pat. Pub. No. US2020/0384434A1 filed on Jun. 7, 2019, with the title "Reversing Bias in Polymer Synthesis Electrode Array."

The anchor sequences attached to the microelectrode array are extended by repeated addition of pre-synthesized oligonucleotide complexes. The oligonucleotide complexes are available in solution to hybridize with the anchor oligonucleotides may be changed during each cycle of assembly. This controls "what" is added to the oligonucleotides attached to the microelectrode array. The selection of which electrodes are negatively charged controls "where" addition does and does not occur. By varying what is added and where additions occur, it is possible to assemble oligonucleotides with different arbitrary sequences at each electrode on the microelectrode array.

Oligonucleotides, also referred to as polynucleotides, include both deoxyribonucleic acid (DNA), ribonucleic acid (RNA), and hybrids containing mixtures of DNA and RNA. DNA includes nucleotides with one of the four natural bases cytosine (C), guanine (G), adenine (A), or thymine (T) as well as unnatural bases, noncanonical bases, and modified bases. RNA includes nucleotides with one of the four natural bases cytosine, guanine, adenine, or uracil (U) as well as unnatural bases, noncanonical bases, and modified bases.

Unless otherwise specified, hybridization as used throughout this disclosure refers to the capacity for hybridization between two single-stranded oligonucleotides or oligonucleotide segments at 21° C. in 1×TAE buffer containing 40 mM TRIS base, 20 mM acetic acid, 1 mM ethylenediaminetetraacetic acid (EDTA), and 12.5 mM $MgCl_2$. Hybridization and washing conditions are well known and exemplified in Sambrook, J., Fritsch, E. F. and Maniatis, T. *Molecular Cloning: A Laboratory Manual, Second Edition*, Cold Spring Harbor Laboratory Press, Cold Spring Harbor (1989), particularly Chapter 11 and Table 11.1 therein; and also in Michael R. Green & Joseph Sambrook, *Molecular Cloning: A Laboratory Manual*, Cold Spring Harbor Laboratory Press, $4^{th}$ ed. (2012). As is known to those of ordinary skill in the art, conditions of temperature and ionic strength determine the "stringency" of the hybridization.

It is understood the sequence of an oligonucleotide need not be 100% complementary to that of its target to be specifically hybridizable. Moreover, the oligonucleotide may hybridize over one or more segments such that intervening or adjacent segments are not involved in the hybridization event (e.g., a loop structure or hairpin structure). The oligonucleotide can comprise at least 20%, 30%, 40%, 50%, 60%, 70%, 80%, 90%, 95%, 99%, or 100% sequence complementarity to a target region within the target oligonucleotide sequence to which they are targeted. The degree to which two oligonucleotides are complementary may also be defined in terms of the number of complementary base pairs. For example, oligonucleotides may be hybridizable if they have at least 5, at least 10, at least 15, at least 20, or more complementary base pairs.

For example, an antisense oligonucleotide in which 18 of 20 base pairs of the antisense compound are complementary to a target region, and would therefore specifically hybridize, would represent 90% complementarity. In this example, the remaining non-complementary nucleotides may be clustered or interspersed with complementary nucleotides and need not be contiguous to each other or complementary nucleotides. As a further example, two oligonucleotides each with 100 nucleotides may hybridize if they share a region in which 20 base pairs are complementary. Percent complementarity between particular stretches of oligonucleotide sequences can be determined routinely using software such as the BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

Figure 1B:
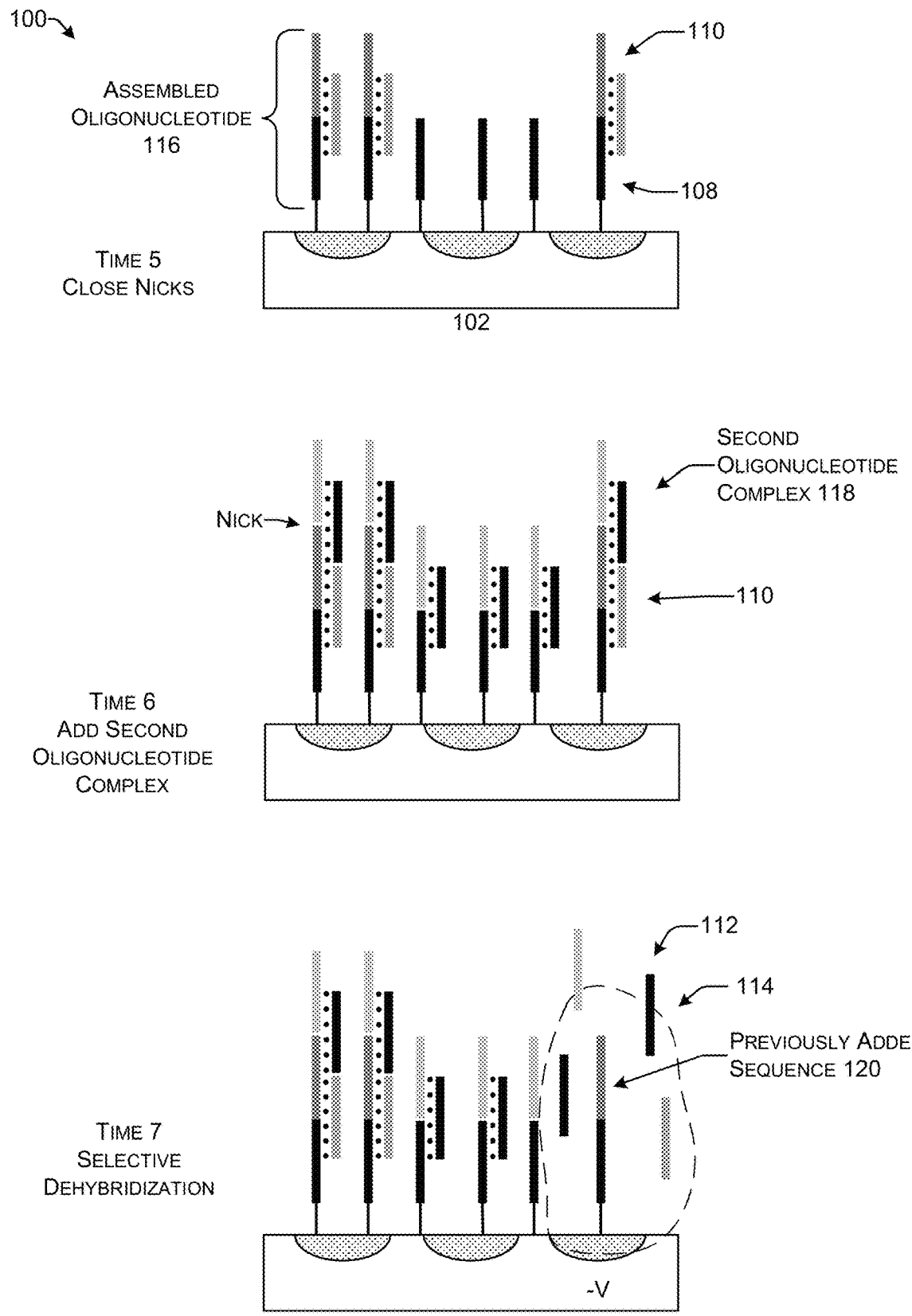
Figure 1C:
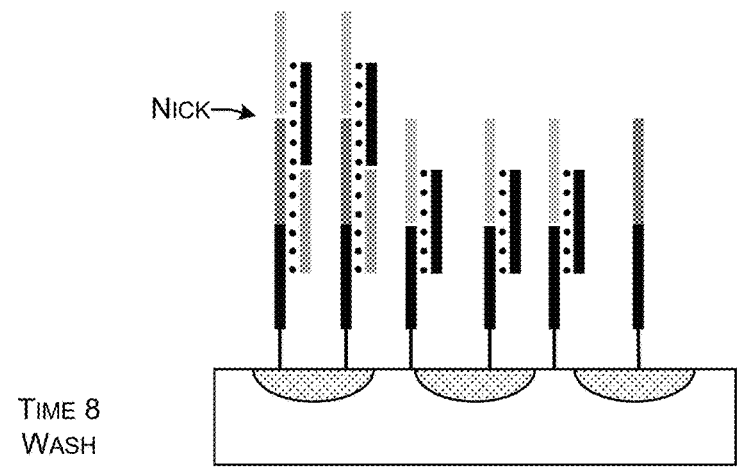
Figure 1C:
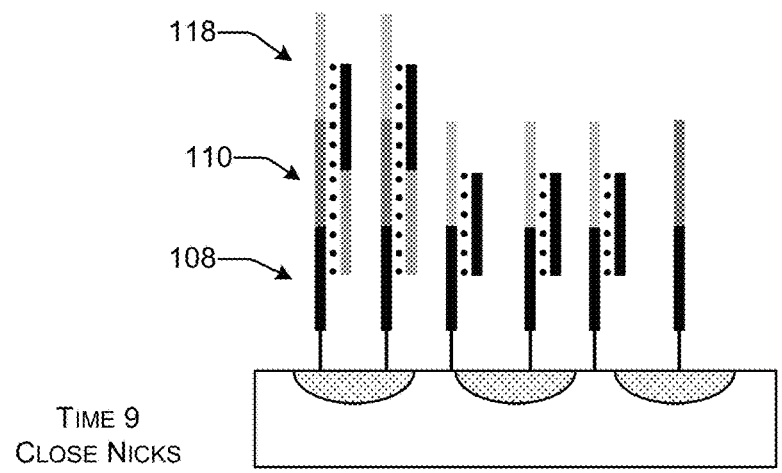

FIGS. 1A-C is an illustrative time series 100 showing creation of oligonucleotides by the combination of multiple oligonucleotide complexes at locations controlled by selective activation of individual electrodes on a microelectrode array 102. The microelectrode array 102 shown in this time series 100 is illustrated with only three electrodes 104 but it is to be understood that the microelectrode array 102 may have many more electrodes 104.

At Time 1, the microelectrode array 102 is shown coated with linkers 106 that are attached to anchor sequences 108 shown here as black bars. The linkers 106 include molecules and structures that attach the anchor sequences 108 to the surface of the microelectrode array 102 such as both linker molecules and functional coatings. In some implementations the linker 106 may be an alkane or alkene change of any length (e.g., C3-C18) that may also be referred to as a spacer. The linkers 106 may be photo-cleavable linkers such as the PC Spacer available as a 5' modification to oligonucleotides available from Integrated DNA Technologies (Iowa, USA) or the PC Linker 26-6888 available from Gene Link (New York, USA). Dithiol or thiol linkers with either 3' or 5' attachment may be used such as the 3' Thiol Modifier C3 S-S linker available from Integrated DNA Technologies. Techniques for attaching various linkers 106 to a solid substrate are well known to those of ordinary skill in the art. The length of the anchor sequences 108 may be between about 5-50, 10-30, 15-20, or 15 nucleotides. All of the anchor sequences 108 on the microelectrode array 102 may have the same nucleotide sequence.

Attachment of the anchor sequences 108 to the surface of the microelectrode array 102 may not correlate in a one-to-one manner with the number or position of electrodes 104. Some electrodes 104 may have more than one anchor sequence 108 attached. Some anchor sequences 108 may be attached to a portion of the microelectrode array 102 that does not include an electrode 104. Some electrodes 104 may have no anchor sequences 108 attached (not shown). However, all anchor sequences 108 attached to the same electrode 104 will be exposed to the same electrochemical environment and generate the oligonucleotides with the same sequence.

At Time 2, a first oligonucleotide complex 110 is added. The first oligonucleotide complex 110 is a partially double-stranded structure shown here by two gray bars. The first oligonucleotide complex 110 may encode a value such as a bit. One of the single-stranded sticky ends of the first oligonucleotide complex 110 hybridizes with the anchor sequence 108. Hybridization resulting in a double-stranded oligonucleotide sequence is indicated by a series of black dots. The hybridization holds the first oligonucleotide complex to an anchor sequence 108. After hybridization, the first oligonucleotide complex 110 is attached to the anchor sequence 108 by base-pairing interactions between the nucleotide bases. Thus, a nick remains in between the end of the anchor sequence 108 and the strand in the first oligonucleotide complex 110 that abuts to the end of the anchor sequence 108. In some implementations, all or substantially all of the anchor sequences 108 may be hybridized to one of the first oligonucleotide complexes 110. At this point, the electrodes 104 in the microelectrode array 102 are not activated.

At Time 3, a first subset of the electrodes 104 is activated. As used herein, "activation" of an electrode 104 refers to causing the electrode 104 to have a negative voltage relative to a reference electrode or to ground that is sufficient to change the local pH such that double-stranded oligonucleotides de-hybridize. This causes the first oligonucleotide complexes 110 attached to the activated electrode 104 to disassociate into single-stranded oligonucleotides 112. FIG.

1A illustrates the middle electrode generating a negative voltage. The current creates a basic environment 114 proximate to the electrode 104. Although only one electrode 104 is shown as activated, any or all of the electrodes 104 may be activated at a given time.

The specific voltage used in a given system will depend on the electrode size and type of electrode array as well as the buffer conditions. The voltage may be between about −1 V to −5 V. In some implementations, the voltage may be between about −1 V and −2 V such as about −1.0 V, −1.1 V, −1.2 V, −1.3 V, −1.4 V, −1.5 V, −1.6 V, −1.7 V, −1.8 V, −1.9 V, or −2.0 V. The voltage may be maintained for a period of time sufficient for de-hybridization to occur. The period of time may be between about 30 seconds and 2 minutes such as about 30 seconds, 45, seconds, 60 seconds, 75 seconds, 90 seconds, 105 seconds, or 120 seconds. The surface of the microelectrode array 102 is covered with an electrically conductive buffer solution that may be aqueous or mixed aqueous/organic. The buffer solution may have a neutral pH of between about 6 and 8.5. For example, the buffer solution may have a pH of about 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, or 8.5. The concentration of the buffer may be between about 0.01 and 0.1 M, such as about 0.01, 0.02, 0.03, 0.04, 0.05, 0.06, 0.07, 0.08, 0.09, or 0.1 M.

The buffer may be any type of buffer that is compatible with oligonucleotides and that is electrically conductive. In implementations, the buffer may be a salt buffer, a brine solution, or a phosphate buffer. Examples of salt buffers include $(NH_4)2SO_4$, $Na_2SO_4$, NaCl, KCl (potassium chloride) and $CH_3COONH_4$. Brine is a high-concentration solution of salt (NaCl) in water ($H_2O$). In different contexts, brine may refer to salt solutions ranging from about 3.5% up to about 26%. Phosphate buffers include potassium phosphate buffers and sodium phosphate buffers. Potassium phosphate buffers consist of a mixture of monobasic dihydrogen phosphate and dibasic monohydrogen phosphate. Potassium phosphate buffers have excellent buffering capacity and are highly soluble in water. Sodium phosphate buffer also called phosphate-buffered saline (abbreviated PBS) is a water-based salt solution containing disodium hydrogen phosphate, sodium chloride, and in some formulations potassium chloride and potassium dihydrogen phosphate.

As will be appreciated by those of ordinary skill in the art, the starting pH of the buffer, buffer concentration, and applied voltage all interact to determine how much the pH of the buffer solution changes when an electrode 104 is activated. The area of effect, or the distance from the surface of an active electrode 104 where the pH change occurs, is also affected by the combination of buffer pH, buffer concentration, and voltage. Persons of ordinary skill in the art will be able to readily determine through standard electrochemistry principles the area of effect for a given system. The conditions of the system may be tuned accordingly so that the negative voltage of an activated electrode creates a localized increase in pH sufficient to cause de-hybridization of double-stranded oligonucleotides. The localized increase in pH is created in proximity to an activated electrode 104 without causing de-hybridization of oligonucleotides attached to adjacent electrodes 104.

At Time 4, an optional wash step may remove the single-stranded oligonucleotides 112. The wash step may be performed with a wash buffer that may be the same as the buffer used to deliver the first oligonucleotide complex 110. In some implementations, a separate wash step may be omitted and the single-stranded oligonucleotides 112 are removed when the next oligonucleotide complexes are added. The negative voltage may be maintained at the activated electrode 104 during the wash step or the voltage may be stopped.

At Time 5, nicks between the first oligonucleotide complexes 110 hybridized to the anchor sequences 108 are closed. At this point, nicks in the backbone of the oligonucleotides have not been closed. Nicks in an oligonucleotide backbone may be closed by ligation. Techniques for performing ligation and closing of nicks in DNA and RNA are well-known to those of ordinary skill in the art. Closing of the nicks creates a covalent bond between the anchor sequences 108 one of the strands of the first oligonucleotide complexes 110 forming assembled oligonucleotides 116.

Ligases for both DNA and RNA are known. DNA ligase is a specific enzyme that joins DNA strands together by catalyzing the formation of a phosphodiester bond. One specific type of DNA ligase that is frequently used in molecular biology is T4 DNA Ligase isolated from bacteriophage T4. T4 DNA ligase is most active at 37° C. RNA ligase (ATP) is an analogous enzyme that catalyzes the formation of phosphodiester bonds between ribonucleotides. One commercially available RNA ligase suitable for closing nicks is T4 RNA ligase 2. T4 RNA ligase 2 is also most active at 37° C.

However, for optimal ligation efficiency with sticky ends, the optimal temperature for the enzyme is balanced with the melting temperature $T_m$ of the sticky ends being ligated because the homologous pairing of the sticky ends may be disrupted by high temperatures. If any of the sticky ends in the double-stranded oligonucleotide structure shown at Time 5 would be disrupted at optimal temperatures for the selected ligase, a lower temperature may be used. Persons of ordinary skill in the art will understand how to calculate $T_m$ for a given oligonucleotide structure and adjust the ligation temperature appropriately.

Another technique for closing nicks uses click chemistry to form covalent bonds between nucleotides with modified 3-end 5'-ends. One click-chemistry reaction that may be used is Copper(I)-catalyzed azide-alkyne cycloaddition (CuAAC) also referred to as azide-alkyne Huisgen cycloaddition. With this reaction, an alkyne and an azide group are joined by a cycloaddition reaction to form a triazole unit that becomes the backbone connecting adjacent nucleotides. This reaction is triggered by addition of copper(I). Use of CuAAC to join DNA strands is discussed in El-Sagheer and Brown, *Click Nucleic Acid Ligation: Applications in Biology and Nanotechnology,* 45(8) Accounts of Chem. Res. 1258 (2011).

At Time 6, a second oligonucleotide complex 118 shown here by a light gray bar and a black bar is contacted with the surface of the microelectrode array 102. The second oligonucleotide complex 118 may encode a different value than the first oligonucleotide complex 110 such as a different bit. Alternatively, it may encode the same value. Sticky ends on the second oligonucleotide complex 118 may hybridize to either anchor sequences 108 or the first oligonucleotide complexes 110 already attached to the microelectrode array 102. Nicks now exist between the second oligonucleotide complexes 118 and the oligonucleotide strands to which they have hybridized. Addition of the second oligonucleotide complexes 118 may displace any single-stranded oligonucleotides 112 remaining from time 3.

At Time 7, a different electrode 104 is activated with a negative voltage. This causes the oligonucleotide complexes to de-hybridize and detach. In this example illustration, the second oligonucleotide complex 118 added at time 6 and first oligonucleotide complex 110 added at time 2 both de-hybridize. This leaves the previously added sequence 120 from the first oligonucleotide complex 110 attached to the anchor sequence 108 at the activated electrode.

At Time 8, there may be an optional wash step. The wash step may be the same as the wash step at time 4.

At Time 9, nicks are closed between second oligonucleotide complexes 118 and the first oligonucleotide complexes 110 and anchor sequences 108. Closing of the nicks may be performed in the same way as at time 5. This process may be repeated, iteratively adding additional oligonucleotide complexes to locations on the microelectrode array 102 where the electrodes 104 are not activated.

Figure 2:
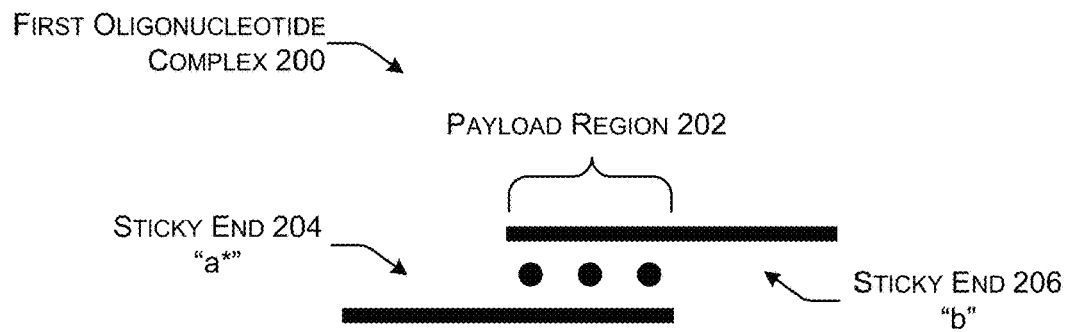
FIG. 2 illustrates configurations of multiple types of oligonucleotide complexes.
Figure 2:
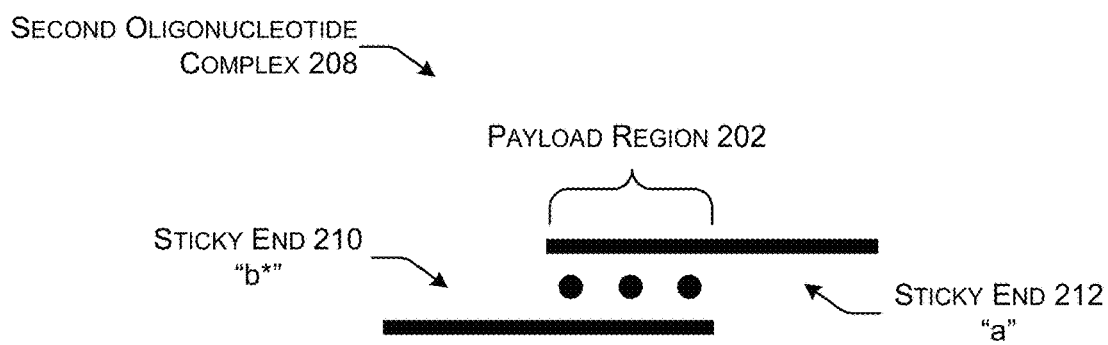
Figure 2:
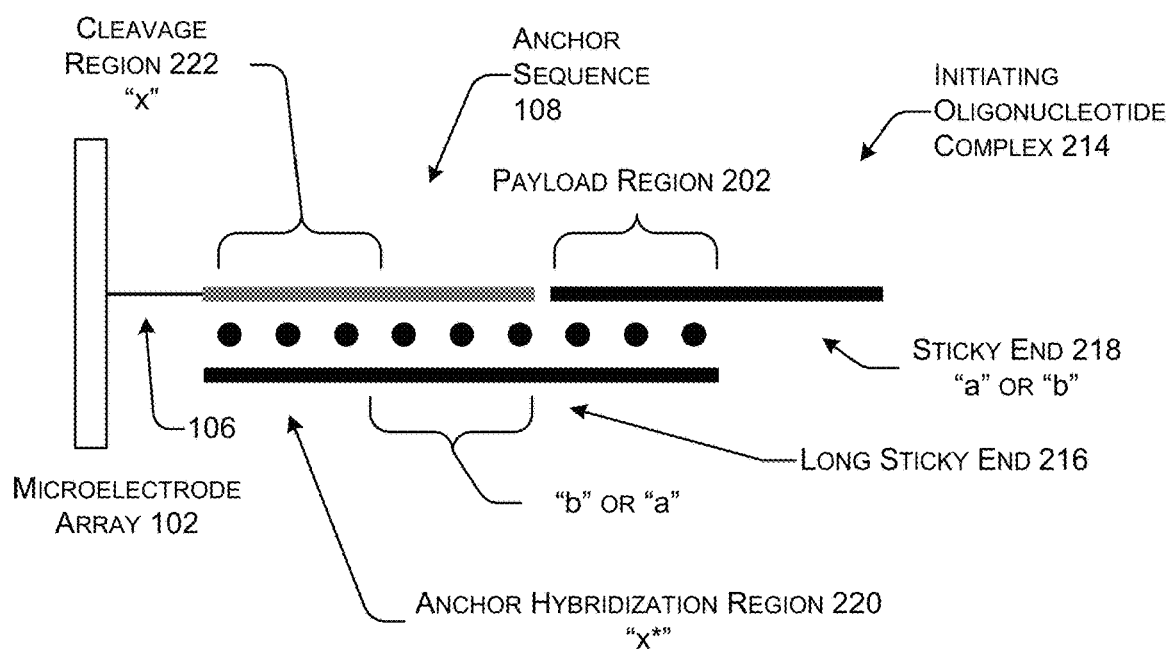

FIG. 2 illustrates configurations of multiple types of oligonucleotide complexes. A first oligonucleotide complex 200 includes a payload region 202 which is the double-stranded region in the middle, although not necessarily centered between the two sticky ends 204 and 206. The payload region 202 may be any length for example between about 1-50 nucleotides, about 10-20 nucleotides, or about 15 nucleotides. The sequence of the payload region 202 may encode an arbitrary value such as a binary digit or a bit with an example encoding of CTA=1 and ACG=0. The payload region 202 may encode trits, letters of the English alphabet, or any other arbitrary value. The number of different variations of the payload region 202 may depend on the number of different values that are encoded (e.g., two different payload regions for encoding bits, 26 different payload regions for encoding letters of the English alphabet, etc.). In some implementations, the payload region 202 may also encode sequences with biological meaning such as portions of a gene.

In the first oligonucleotide complex 200, the payload region 202 is flanked by the first sticky end 204 and a second sticky end 206. The sticky ends 204 and 206 are not complementary to each other. If they were complementary, oligonucleotide complexes 200 could hybridize with each other in solution forming rings or other structures and preventing efficient hybridization with the anchor sequences 108. The sticky ends 204, 206 may be the same length or different lengths and may be any length for example between about 5-30 nucleotides, about 10-20 nucleotides, or about 15 nucleotides. Thus, the total length of one single-stranded oligonucleotide in an oligonucleotide complex 200 may be about 6-80 nucleotides, about 15-60 nucleotides, or about 30-45 nucleotides.

The first sticky end 204 is denoted in the figures as "a*" and the second sticky end 206 is denoted as "b." The notation of n* indicates a sequence that hybridizes to or is complementary to n where n represents a single-stranded oligonucleotide sequence. Thus, a* is complementary to a, b* is complementary to b, and so forth.

The second oligonucleotide complex 208 shown in FIG. 2 contains the same payload region 202 but with a first alternate sticky end 210 (e.g., b*instead of b) and a second alternate sticky end 212 (e.g., a* instead of a) that are complementary to the sticky ends 204 and 206 of the first oligonucleotide complex 200. The oligonucleotide complex 208 may be referred to as an alternate configuration of the first oligonucleotide complex 200 or as a complementary oligonucleotide complex because it encodes the same information (same payload region 202) but has different sticky ends 210 and 212.

If a washing step is included between rounds of assembly, the two complementary oligonucleotide complexes 200, 208 are generally not in solution together. This may prevent the first oligonucleotide complex 200 and the second oligonucleotide complex 208 from hybridizing to each other in solution. However, after either of the oligonucleotide complexes 200, 208 are hybridized to anchor sequences 108 and nicks are close making a covalent attachment, they will remain after washing and provide a single-stranded sequence that can hybridize with the next oligonucleotide complex. Because the oligonucleotide complexes 200, 208 are designed so they do not hybridize to themselves, the same oligonucleotide sequence cannot be added in two sequential cycles. In order to add the same payload region 202 twice complementary oligonucleotide complexes are used as explained below.

If the same payload region 202 is to be added twice, for example to encode the binary string 00, the oligonucleotide complex 200 cannot be used to add the second 0 because the two sticky ends 204 and 206 are noncomplementary. If the sticky end with the sequence a* hybridizes to an anchor sequence 108, then the available sticky end for the next oligonucleotide complex to hybridize will have sequence b. But oligonucleotide complex 200 does not have a sticky end with the complementary sequence of b*. Thus, the complementary oligonucleotide complex 208 has a sticky end 210 with sequence b* is used. To create a long string of the same payload region 202, the alternate versions of an oligonucleotide complex 200, 208 are added alternately for each round of assembly.

In some implementations, the oligonucleotide complex that hybridizes to the anchor sequence 108, the "initiating oligonucleotide complex" 214, may be different than oligonucleotide complexes used later in assembly. The initiating oligonucleotide complex 214 is a partially double-stranded structure and may have a long sticky end 216 that hybridizes to the anchor sequence 108 and a regular-length sticky end 218. The long sticky end 216 may hybridize to the full length of the anchor sequence 108. The long sticky end 216 may include a region that has the same sequence as a sticky end of other oligonucleotide complexes 200, 208 (e.g., an "a," "b," "a*," or "b*" sequence) and an anchor hybridization region 220 "x*" that hybridizes to a cleavage region 222 in the anchor sequence 108 denoted as "x". Use of a long sticky end 216 creates a longer region of hybridization with the anchor sequence 108 which can increase stability. However, the long sticky end 216 does not necessarily include a region that hybridizes to a sticky end (i.e., no "a" or "b" sequence) and may instead include the anchor hybridization region 220 alone or together with a nucleotide sequence that hybridizes only to the anchor sequence 108.

The long sticky end 216 can create a double-stranded region that is not found elsewhere. This double-stranded region is formed from the hybridization of the cleavage region 222 and the anchor hybridization region 220 and may be located at or near the base of the anchor sequence 108 as shown in FIG. 2. This cleavage region 222 provides a unique double-stranded sequence for recognition and cleavage by enzymes such as Type II restriction enzymes or Cas9. Thus, a length of the cleavage region 222 may be at least a length sufficient to be recognized by an endonuclease such as, for example at least four, five, six, seven, eight, nine, or 10 nucleotides. Enzymatic cleavage of the anchor sequence 108 is one technique for separating completed oligonucleotides from the microelectrode array 102.

Figure 3:
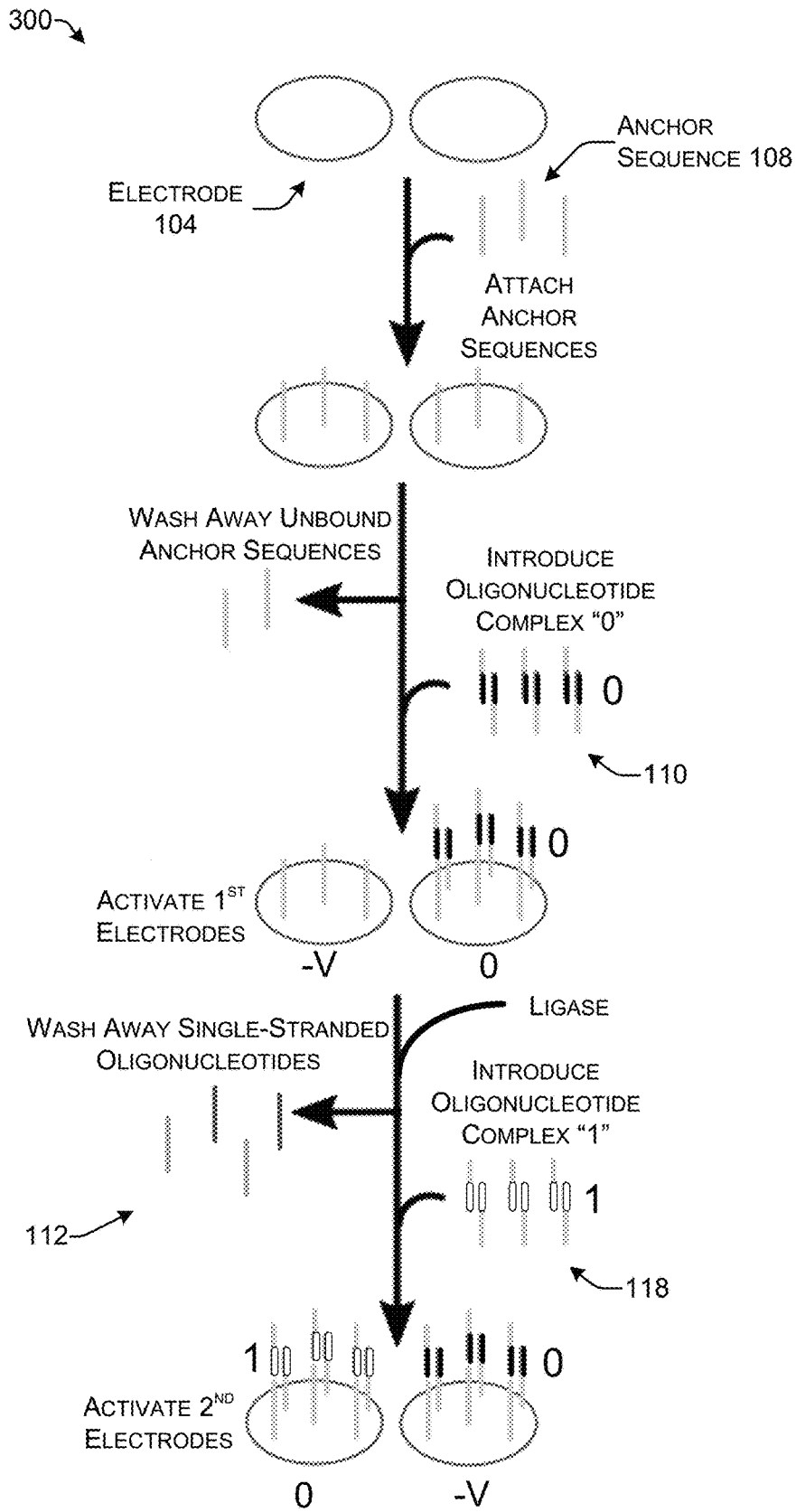
FIG. 3 illustrates a series of steps used to encode arbitrary values at specific locations on the surface of a microelectrode array through the use of multiple oligonucleotide complexes.

FIG. 3 shows a schematic illustration 300 of a series of steps that may be used to encode arbitrary values at specific electrodes 104 on a microelectrode array 102. Prior to selective assembly of oligonucleotides on a microelectrode array 102, the anchor sequences 108, shown here as gray bars, are attached to electrodes 104 on the surface of the microelectrode array 102. The anchor sequences 108 may be created by any known technique for oligonucleotide synthesis and attached to the electrodes 104 by any known technique for anchoring single-stranded oligonucleotides to a solid substrate. Unbound anchor sequences 108 that remain in solution may be washed away during a washing step that may flood the surface of the microelectrode array 102 with water or a predominantly aqueous solution such as a buffer.

In this example, the first oligonucleotide complex 110 introduced to the surface of the microelectrode array 102 encodes the bit "0." However, the payload region of this oligonucleotide complex 110 may, of course, encode a sequence representing any other arbitrary value. Selective activation of electrodes 104 with a negative voltage causes de-hybridization of the oligonucleotide complexes 110 and disassociation from the anchor sequences 108. Thus, the oligonucleotide complexes 110 remain hybridized to only those electrodes that have are not activated. Thus, although the first oligonucleotide complex 110 is present in solution across the entire surface of the microelectrode array 102, it hybridizes in appreciable amounts only to those anchor sequences 108 not attached to activated electrodes 104.

A subsequent optional washing step washes away any single-stranded oligonucleotides 112 resulting from the de-hybridization. Thus, only those oligonucleotide complexes 110 that have hybridized to an anchor sequence 108 remain. As discussed above, hybridization does not require fully complementary sequences but only that the strength of attachment between the oligonucleotide complexes 110 and the anchor sequences 108 is sufficient to hold the oligonucleotide complexes 110 in place during the washing step.

Ligase may be added to close nicks between the oligonucleotide complexes 110 and the anchor sequences 108.

Next, in this example, a second oligonucleotide complex 118 is introduced. This oligonucleotide complex 118 encodes the bit "1." This second oligonucleotide complex 118 has sticky ends with sequences such that it may hybridize either to the anchor sequences 108 or to the free sticky ends on the first oligonucleotide complexes 110. The location of hybridization is controlled by activation of the electrodes. In this example, a different subset of electrodes is activated after the second oligonucleotides complex 118 is added. Thus, the second oligonucleotide complex 112 hybridizes to different anchor sequences 108 than the first oligonucleotide complex 110.

Although only two electrodes 104 are shown in this example, this technique of selectively activating specific sets of electrodes 104 while sequentially providing oligonucleotide complexes 110, 118 may be used to create assemblies of oligonucleotide complexes 110, 112 on the surface of individual electrodes 104. Thus, different oligonucleotide sequences each encoding an arbitrary string of bits may be created at each electrode 104.

Figure 4:
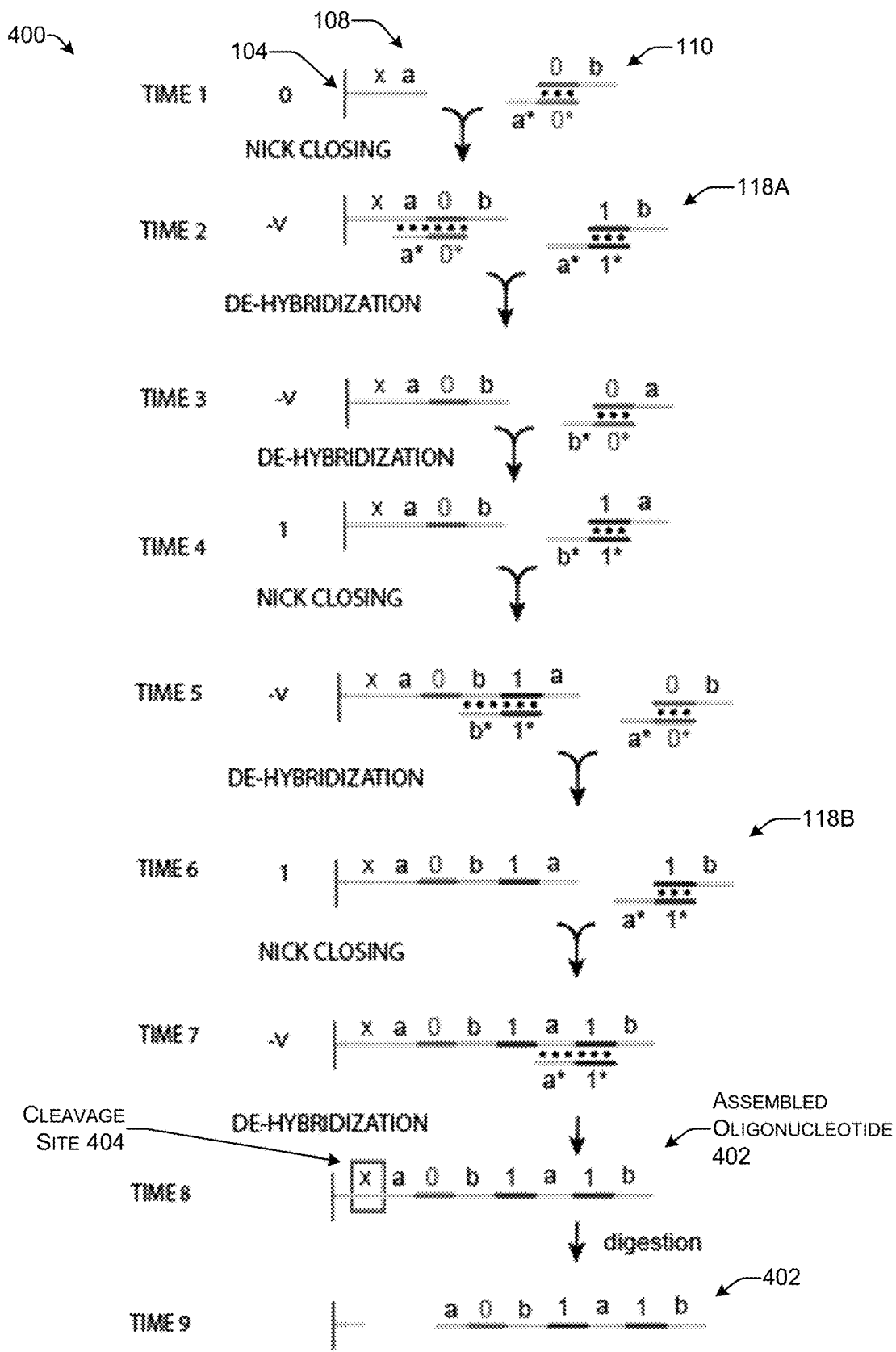
FIG. 4 illustrates a series of steps used to assemble an oligonucleotide that encodes a string of arbitrary values and to separate the assembled oligonucleotide from the surface of a microelectrode array.

FIG. 4 shows a time series 400 of a series of steps that may be used to encode a string of arbitrary values in an oligonucleotide by creating an ensemble of oligonucleotide complexes. This time series 400 continues with the example of FIG. 3 that uses oligonucleotide complexes to encode bits; however, the principles are the same for encoding other types of data. Selective activation of electrodes 104 during the rounds of addition controls the particular sequence of bits encoded at a given location on the microelectrode array. FIG. 4 shows the steps of building an oligonucleotide on only a single electrode 104. The same steps may be repeated for other electrodes 104 on a microelectrode array 102 to create in parallel multiple oligonucleotides with different sequences.

At Time 1, an anchor sequence 108 with the sequence represented by "x a" is shown attached to the electrode 104. A first oligonucleotide complex 110 is introduced. The first oligonucleotide complex 110 encodes the bit "0." Complementary base sequences between a sticky end (a*) and the end of the anchor sequence 108 (a) cause the first oligonucleotide sequence to hybridize to the anchor sequence 108. The electrode 104 is not activated at this time. In some implementations, this may be an initiating oligonucleotide complex as shown in FIG. 2. An initiating oligonucleotide complex will have a longer overhang that also hybridizes with the x portion of the anchor sequence 108.

Addition of the first oligonucleotide complex is followed by nick closing that creates a covalent bond between one strand (i.e., the 0 b strand on "top") and the anchor sequence 108. Nick closing may also happen simultaneously or substantially simultaneously with the addition of the oligonucleotide complex. For example, the first oligonucleotide complex 110 and the enzyme ligase may be added together.

At Time 2, a first version of a second oligonucleotide complex 118A encoding the bit "1" is introduced. Also, at time 2 the electrode is activated with a negative charge. The negative charge increases the pH to a level sufficient to cause de-hybridization of double-stranded oligonucleotides. The elevated (more basic) pH results in the second oligonucleotide complex 118A separating into two single-stranded oligonucleotides and disassociation of the strand from the first oligonucleotide complex that remains hybridized to the anchor sequence 108 (i.e., the a* 0* strand on "bottom"). Thus, the other strand from the first oligonucleotide (i.e., the 0 b strand) remains attached to the anchor sequence 108 because of the covalent bond following the nick closing.

Although the first version of the second oligonucleotide complex 118A is not added to the anchor sequence 108 at this electrode 104 it may be added elsewhere. On a microelectrode array with thousands or more individually-addressable electrodes, during each round of oligonucleotide complex addition there will likely be some electrodes where a given oligonucleotide complex is added and some where it is not.

At Time 3 the first oligonucleotide complex 110 is introduced again. However, because the negative voltage is maintained at the electrode 104 it cannot hybridize to the extended anchor sequence 108. The first oligonucleotide complex 110 de-hybridizes in proximity to the electrode 104 due to the basic pH.

At Time 4, the first version of the second oligonucleotide complex 118A is again added and the electrode 104 is no longer activated. The first version of the second oligonucleotide complex 118A hybridizes to the end of the extended anchor sequence (i.e., b to b*). This adds the bit "1" to the growing oligonucleotide. This is followed or accompanied by nick closing.

At Time 5, the first oligonucleotide complex 110 is added again but because a negative voltage is maintained at the electrode 104, the elevated pH prevents hybridization to the extended anchor sequence 108. The elevated pH also causes the remaining doubled-stranded portion of the first version of the second oligonucleotide complex 118A (i.e., the b*1*strand) to de-hybridize.

At Time 6, a second version of the second oligonucleotide complex 118B is that also encodes the bit "1" is added and the electrode 104 is not activated so hybridization is possible. The first and second versions of the second oligonucleotide complex 118 include the same payload region encoding the same arbitrary value of "1" but have different sticky ends. The difference in the sticky ends makes it possible for the sticky end "a*" on the second version of the second oligonucleotide complex 118B to hybridize with the available sticky end "a" on the first version of the second oligonucleotide complex 118A. Thus, by using two different versions of the second oligonucleotide complex 118 the same bit (i.e., "1") can be added twice. Again, addition of this oligonucleotide complex is followed or accompanied by nick closing.

This process of sequentially adding oligonucleotide complexes that encode arbitrary values such as 0 or 1 may be repeated until the desired sequence of data (e.g., a string of bits) is represented in the oligonucleotide. In this example, the bits "0" and "1" are introduced alternatively to the microelectrode array. After a round of adding oligonucleotide complexes encoding the bit "0" the next round adds oligonucleotide complexes encoding the bit "1" which is in turn again followed by addition of the bit "0."

At Time 7, a final de-hybridization step may be performed without addition of any oligonucleotide complexes. Activation of the electrode 104 creates a localized basic environment that causes any remaining doubled-stranded structures to de-hybridize. This leaves a single-stranded, assembled oligonucleotide 402 attached to the surface of the microelectrode array. The final de-hybridization may be followed by a wash step to remove any oligonucleotides that are free in solution.

At Time 8, the assembled oligonucleotide 402 may be released from the surface of the microelectrode array by digestion with an endonuclease. A cleavage site 404 (sequence x) at the base of the anchor sequence 108 may be cleaved by using known techniques for digestion of single-stranded oligonucleotides such as with the enzyme USER® (Uracil-Specific Excision Reagent) available from New England BioLabs, Xcml or divergent Cas9 enzymes (Enbo Ma et al., *Single-stranded DNA cleavage by divergent CRISPR-Cas9 enzymes,* 60(3) Mol Cell. 398-407 (2015)). In other implementations, a linker attaching the anchor sequence 108 to the microelectrode array (e.g., linker 106 from FIG. 1) may be cleaved instead of the anchor sequence 108 itself.

At Time 9, the assembled oligonucleotide 402 is freed from the electrode 104. A string of binary digits (e.g., 011) is encoded in the order of payload sequences encoded in the assembled oligonucleotide 402. The assembled oligonucleotide 402 may be cleaned, purified, and/or amplified by polymerase chain reaction (PCR) to create additional copies. It may be stored as a molecular record of the binary digits. Thus, the assembled oligonucleotide 402 may function as a medium for storing digital data. The information or data encoded in the assembled oligonucleotide 402 may be read by sequencing using any conventional oligonucleotide sequencing technique.

Figure 5:
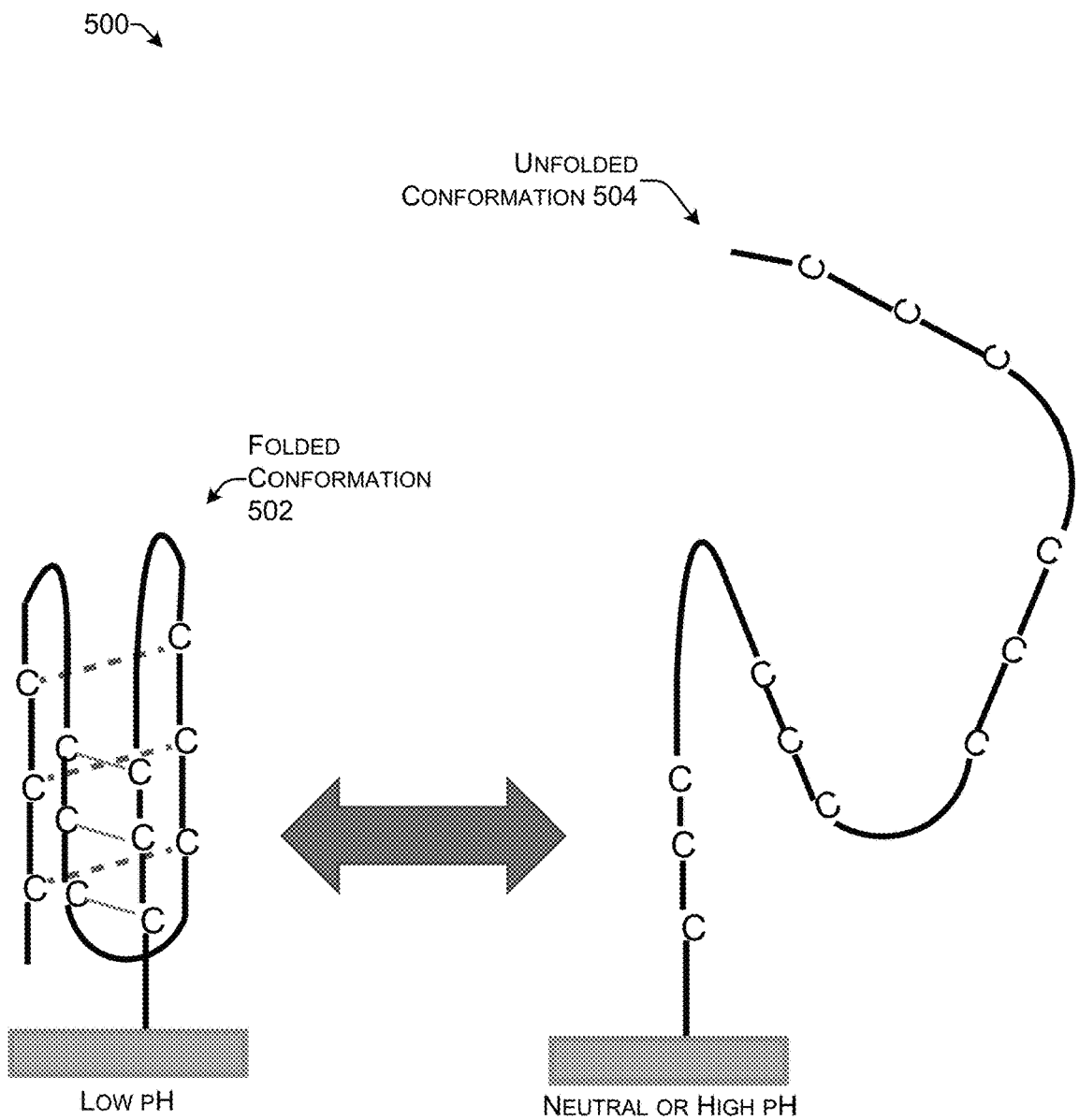
FIG. 5 illustrates conformational changes in an i-motif sequence based on pH that is used to control where oligonucleotide complexes can hybridize on the surface of a microelectrode array.

FIG. 5 is a diagram 500 showing the pH-dependent conformational change of an i-motif sequence. i-Motif sequences consist of antiparallel tracts of oligodeoxynucleotides strands that contain mostly cytosine residues. The interactions between these molecules occur by the hemi protonation of cytosine residues and non-Watson Crick base pairing, more specifically Hoogsteen base pairing. i-Motifs are described in Adam et al., Electrochemical Monitoring of the Reversible Folding of Surface-Immobilized DNA i-Motifs, *Langmuir,* Vol. 34, 3112-3118 (2018).

The conformational changes from a folded conformation 502 at low pH to an unfolded conformation 504 at neutral or high pH provide an alternative technique for site-specific regulation of oligonucleotide complex binding. The anchor sequences or sticky ends of oligonucleotide complexes may include i-motif sequences. These single-stranded regions are able to hybridize with complementary oligonucleotides only when in the unfolded conformation 504. FIG. 5 illustrates an i-motif sequence attached to a solid substrate such as a linker sequence attached to a microelectrode array. The linker sequence may be inactivated or made unable to hybridize with oligonucleotide complexes by reducing the pH so that it forms an i-motif. Similarly, if one or more sticky ends of an oligonucleotide complex contain i-motifs, low pH will prevent those oligonucleotide complexes from hybridizing with complementary sequences.

i-Motif sequences are cytosine (C) rich oligonucleotide sequences that take on a folded conformation 502, the "i-motif," upon protonation of C at low pH. Intramolecular i-motifs result from the folding of particular oligonucleotide single strands upon the protonation of cytosines in sequence leading to the formation of hemiprotonated C—H+—C pairs. The general structure of an i-motif sequence includes four cytosine triple repeats with three other nucleotides between the repeats. The other nucleotides may be any nucleotide besides C. Two i-motif sequences are described in Adam et al.: sequence A (5'-(CCC TAA)$_3$ CCC T-3') is the human telomeric sequence and sequence B (5'-(CCC TTT)$_3$ CCC T-3'). At pH=8.4 (>pH$_{m,so}$l), the DNA strand is unprotonated and in the unfolded state, whereas at pH=5.3 (<pH$_{m,so}$l), it is in the hemiprotonated folded state of the i-motif sequence. i-Motif sequences transition between the folded conformation 502 and the unfolded conformation 504 at about pH=6-8.

The buffer solution may be prepared from 2-(N-morpholino)ethanesulfonic acid (MES monohydrate>99.5), trishydroxymethylaminomethane (Tris, 99.9%), and acetic acid in the molar proportion of 2-1-1 of Tris-MES-acetic acid to an ionic strength of 8.3 mM. After mixing pH may be adjusted using KOH or HClO$_4$ 0.1 M solutions. The buffer mixture (hereafter TMA) was used.

The localized pH proximate to an individual electrode in a microelectrode array may be controlled by changing the voltage. In contrast to the examples that use de-hybridization, for i-motif sequences a positive voltage is used to change the confirmation. The buffer solution is neutral or slightly basic so that the i-motif sequences have an unfolded conformation 502 when electrodes are not activated. Activation of an electrode with a positive voltage creates a localized acidic environment and lowers the pH sufficiently such that i-motif sequences adopt folded conformations 502. The specific voltage will depend on the electrodes used in the microelectrode array and the buffer but may be, for example, about 1-5 V. In some implementations, activation of electrodes with a positive voltage may cause the pH to decrease to about 5.0, 5.1, 5.2, 5.3, 5.4, 5.5, 5.6, 5.7, 5.8, 5.9, or 6.0.

Figure 6:
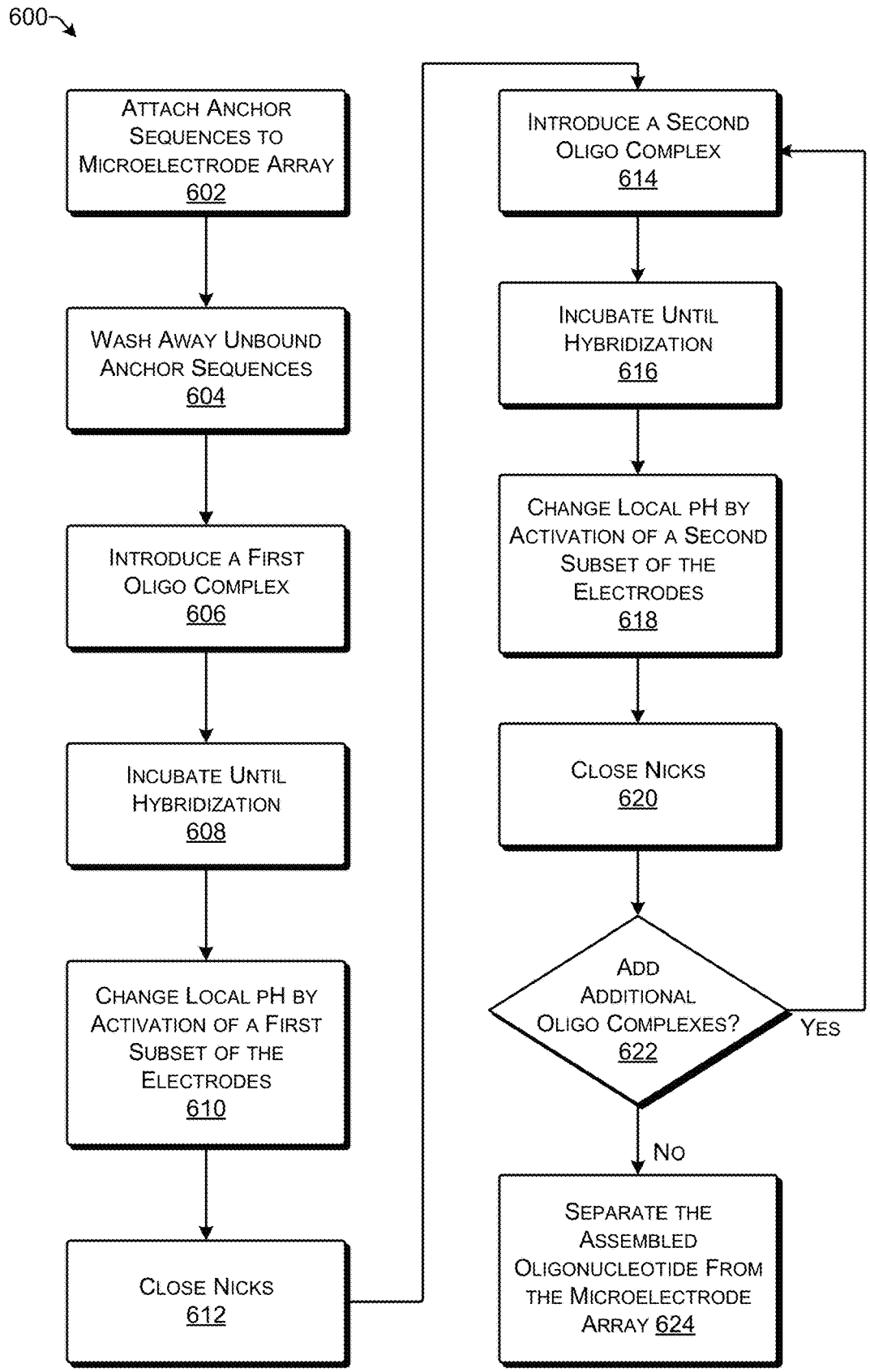
FIG. 6 is a flow diagram showing an illustrative process for assembling an oligonucleotide by joining multiple oligonucleotide complexes together.

FIG. 6 shows process 600 for assembling a double-stranded oligonucleotide by joining multiple oligonucleotide complexes together. Process 600 may be implemented, for example, using any of the techniques or systems shown in FIGS. 1-5.

At operation 602, anchor sequences are attached to a microelectrode array. In an implementation, some or all of the anchor sequences may comprise i-motif sequences as shown in FIG. 5. The anchor sequences may be attached to the microelectrode array by any conventional technique for attaching oligonucleotide sequences to a solid substrate. For example, the surface of the microelectrode array may be coated with linker molecules that in turn attach to an end of the anchor sequences. As a further example, the surface of the microelectrode array may be functionalized through silanization. This creates a microelectrode array that is coated with a plurality of anchor sequences.

At operation 604, unbound anchor sequences are washed away. This removes any anchor sequences that are not attached to the microelectrode array. This washing step may be performed with water or an aqueous wash buffer.

At operation 606, multiple copies of a first oligonucleotide complex are introduced into a reaction chamber containing the microelectrode array. The first oligonucleotide complex has two non-complementary sticky ends and encodes a first arbitrary value such as, for example, a first binary digit such as 0. The first oligonucleotide complex is now present in solution across the surface of the microelectrode array. One of the two non-complementary sticky ends of the first oligonucleotide complex is complementary to and can hybridize with at least a portion of the anchor sequences.

At operation 608, the microelectrode array is incubated with the first oligonucleotide complex so that the first oligonucleotide complex hybridizes with the anchor sequences. Incubation may be performed at a wide range of temperatures so long as the temperature is below the melting temperature of double-stranded oligonucleotides. For example, incubation may be performed at a temperature of about 10-50° C. In one implementation, incubation is performed at room temperature (e.g., about 19-22° C.). Hybridization may begin to occur immediately upon addition of the first oligonucleotide complex. The duration of incubation may be at least 1 minute.

In some implementations, the incubation may be performed for at least 1, 2, 3, 4, 5, 6, 7, 8, 9, or 10 minutes. Incubation may also be performed for longer duration such as about 10-45 minutes. As will be appreciated by those of ordinary skill in the art, the speed of hybridization and the extent to which all available anchor sequences hybridize with one of the first oligonucleotide complexes depends upon the concentration of the oligonucleotide complexes.

At operation 610, hybridization of the first oligonucleotide complex may be inhibited through changing the local pH. Change in the local pH, either creating a localized basic environment or a localized accident environment, may be done by activating a first subset of electrodes on the microelectrode array.

In one implementation, a localized basic environment is created by activating a first subset of electrodes in the microelectrode array. Activation of the electrodes generates a negative voltage that is sufficient to increase the pH such that double-stranded oligonucleotides de-hybridize. For example, the negative voltage may be between about −1 V and −3 V and the pH may be increased to about pH 9 or pH 10. Activation of the first subset of electrodes causes the first oligonucleotide complex to not hybridize at the locations of any of the activated electrodes. The surface of the microelectrode array may be washed while the negative voltage is maintained at the electrodes to displace and remove single-stranded oligonucleotides in solution so that they do not re-hybridize when the electrodes are turned off.

In another implementation, a localized acidic environment is created by activating a first subset of electrodes in the microelectrode array. Activation of the electrodes generates a positive voltage that is sufficient to decrease the pH such that i-motif sequences assume folded conformations. For example, the positive voltage may be between about 1 V and 3 V and the pH may be decreased to about pH 6 or pH 5. Activation of the first subset of electrodes causes the i-motif sequences to fold into i-motif confirmations which prevents hybridization of the oligonucleotide complexes at any of the activated electrodes.

At operation 612, nicks are closed between the anchor sequences the first oligonucleotide complexes. The nicks may be closed by any of the techniques discussed previously such as introducing a ligase into the reaction chamber or initiating Cu(I)-catalyzed azide-alkyne cycloaddition (CuAAC). Closing of the nicks creates a covalent bond between one strand of the first oligonucleotide complex and the anchor sequence.

At operation 614, multiple copies of a second oligonucleotide complex encoding a second arbitrary value are introduced into the reaction chamber. The second oligonucleotide complex includes a sticky end that is homologous to a sticky end of the first oligonucleotide complex that did not hybridize to the anchor sequence (e.g., the free sticky end). The second oligonucleotide complex encodes a second arbitrary value, for example, a second binary digit such as 1. Although this example process 600 describes adding two different arbitrary values in series, it is also possible to add the same arbitrary value repeatedly (e.g., to encode 000 or 111).

At operation 616, the second oligonucleotide complex is incubated with the microelectrode array so that the second oligonucleotide complex hybridizes to the first oligonucleotide complex or the anchor sequences.

At operation 618, hybridization of oligonucleotide complexes is inhibited by activating a second subset of electrodes in the microelectrode array. Activation of the second subset of electrodes creates a localized basic or acidic environment through generating a negative or positive voltage at those electrodes. The localized basic environment is sufficient to increase the pH such that double-stranded oligonucleotides de-hybridize. The localized acidic environment is sufficient to cause i-motif sequences to adopt a folded confirmation. The second subset of electrodes may include electrodes that were activated with the first subset of electrodes at operation 610. Alternatively, the second subset of electrodes may have no overlap with the first subset of electrodes. Activation of the second subset of electrodes prevents the second oligonucleotide complex from hybridizing to anchor sequences or the free sticky ends of the first oligonucleotide complexes.

At operation 620, nicks are closed as in operation 612. Nicks are closed after each cycle of oligonucleotide complex addition.

At operation 622, it is determined if additional oligonucleotide complexes will be added. This determination may be made based on the data to be encoded in oligonucleotide sequences. Additional oligonucleotide complexes may be subsequently added until the desired string of values is represented in the oligonucleotide hybridized to the microelectrode array. For example, in the example shown in FIG. 4, the desired string of values is 011. Once the fourth oligonucleotide complex encoding the final 1 has been added, assembly is complete and there is no need to add additional oligonucleotide complexes.

If the desired sequence has not been fully assembled, then process 600 proceeds along the "yes" path and returns to 614 where a third (fourth, fifth, . . . ) oligonucleotide complex with alternate sticky ends is introduced to the reaction chamber. A third subset of electrodes is subsequently activated controlling where the third oligonucleotide complex does not attach. Repeated cycles of adding nucleotide complexes and activating selected subsets of electrodes enable the creation of multiple different oligonucleotides with specified sequences of the arbitrary values encoded by the oligonucleotide complexes. If, however, no more oligonucleotides will be added, process 600 proceeds along the "no" path to 624.

At operation 624, the assembled oligonucleotides are separated from the microelectrode array. All assembled oligonucleotides attached to the surface of the microelectrode array may be separated in the same operation. Thus, in an implementation, separation of the assembled oligonucleotides is not selective.

There are multiple ways to separate an oligonucleotide from a solid substrate. The support-bound oligonucleotide may be treated with ammonia to cleave a linker. Depending on the type of linker, the treatment may be exposure to gaseous ammonia, aqueous ammonium hydroxide, aqueous methylamine, or a solution of ammonia in anhydrous methanol. Enzymatic cleavage may be used to cut a portion of the anchor sequence as shown in FIG. 4. Cleavage of a linker attaching the anchor sequence to the microelectrode array may be used to separate the assembled double-stranded oligonucleotide (together with anchor sequence) from the microelectrode array. Cleavable linkers and techniques for cleaving such linkers are known to those of ordinary skill in the art.

Following separation from the microelectrode array, the assembled oligonucleotide may be processed further such as, for example, by amplification with PCR. The PCR product may be stored for short or long term. The sequence of arbitrary values encoded in the double-stranded oligonucleotide may be obtained by sequencing the assembled oligonucleotide and/or PCR amplification products.

Figure 7:
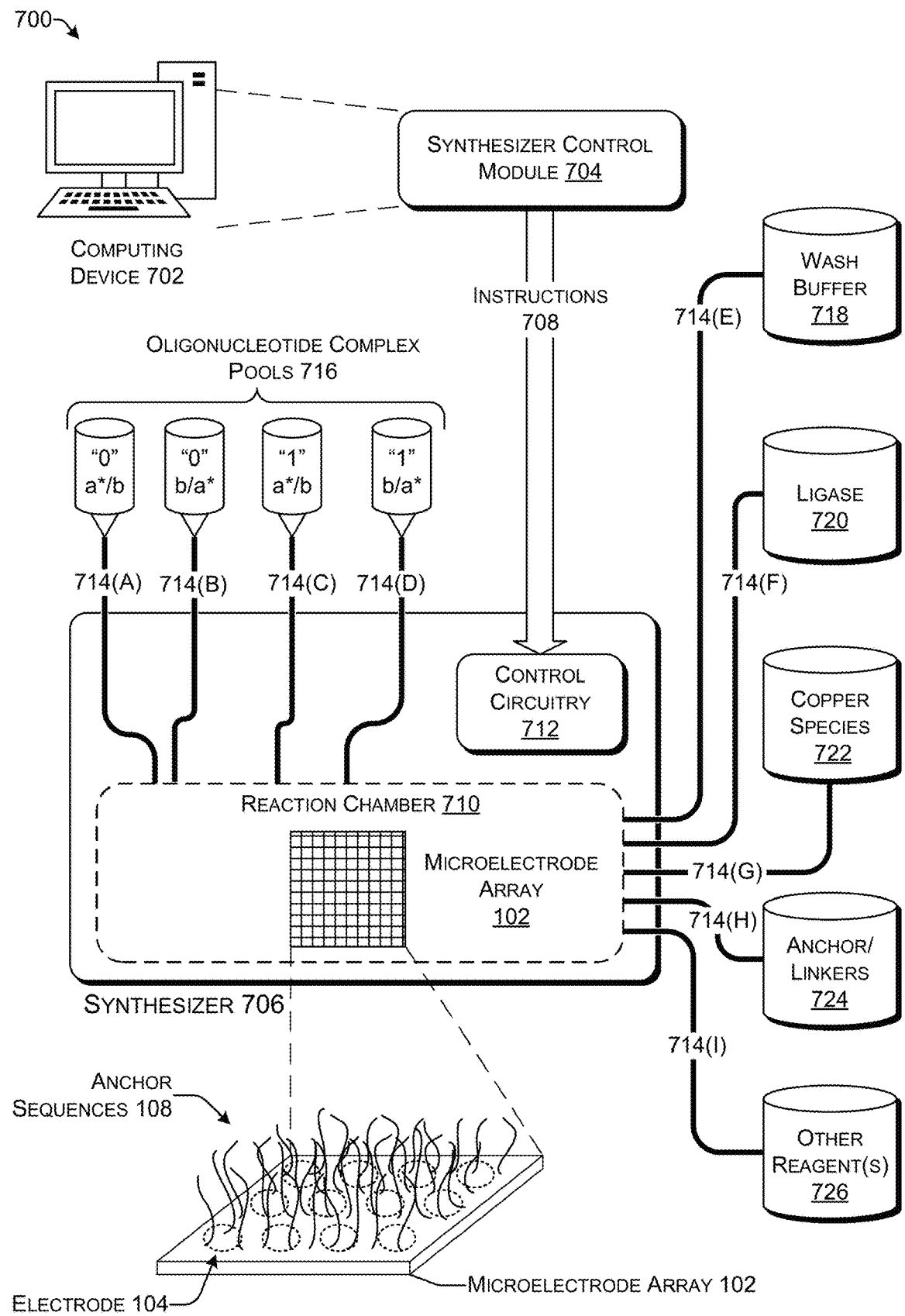
FIG. 7 is an illustrative system for creating oligonucleotides by joining multiple oligonucleotide complexes together.

FIG. 7 shows an illustrative system 700 that may include a computing device 702 with a synthesizer control module 704 that is communicatively connected to a synthesizer 706. The synthesizer control module 704 may provide instructions 708 that control the operation of the synthesizer 706. The instructions may cause the synthesizer 706 to create oligonucleotides with specific sequences and/or that encode specific information. The computing device 702 may be implemented as any type of conventional computing device such as a desktop computer, a laptop computer, a server, a hand-held device, or the like. In an implementation, the computing device 702 may be a part of the synthesizer 706 rather than a separate device.

The synthesizer 706 is a device that selectively assembles oligonucleotides through pH based electrode controlled hybridization. The microelectrode array 102 may be located within a reaction chamber 710 or container capable of maintaining an aqueous or predominantly aqueous environment in contact with the surface of the microelectrode array 102.

As described above, the microelectrode array 102 includes a plurality of electrodes 104 that are able to be independently activated to vary the charge across the surface of the microelectrode array 102. The anchor sequences 108 may be synthesized directly onto silane groups attached to the microelectrode array 102 using standard phosphoramidite reagents and methods. After preparation by this, or another, technique, the microelectrode array 102 coated with a plurality of anchor sequences may be placed in the synthesizer 706. The microelectrode array 102 may be held in a jig that creates a seal around the edges of the microelectrode array 102 preventing fluid from the reaction chamber 710 from contacting the sides or bottom of the microelectrode array 102.

Control circuitry 712 may control the operation of the synthesizer 706. The control circuitry 712 may be implemented as any type of circuitry suitable for controlling hardware devices such as a printed circuit board, microcontroller, a programmable logic controller (PLC), or the like. The control circuitry 712 receives the instructions 708 provided by the synthesizer control module 704. Instructions 708 may indicate the final sequences of assembled oligonucleotides to be assembled at individual electrodes 104 on the microelectrode array 102. The instructions 708 may specify the sequence information as an ordered sequence of values (e.g., 00101 . . . ) including at least a first arbitrary value (e.g., "1") and a second arbitrary value (e.g., "0").

The control circuitry 712 may be able to independently control the voltage at each of the electrodes 104 in the microelectrode array 102. Specifically, control circuitry 712 may be configured to selectively generate negative voltages sufficient to increase the pH such that double-stranded oligonucleotides de-hybridize in proximity to individual electrodes 104 in the microelectrode array 102. In some implementations, the control circuitry 712 may implement a not logic because activation of electrodes results in oligonucleotide complexes being unable to hybridize at the activated electrodes. For example, the instructions 708 may indicate the locations on the surface of the microelectrode array 102 where oligonucleotides should be extended and the control circuitry 712 may use a not logic to activate electrodes other than at areas where the oligonucleotides are to be extended.

The control circuitry 712 may also be able to selectively open and close fluid delivery pathways 714 to control the movement of fluids throughout the synthesizer 706 including in the reaction chamber 710. The fluid delivery pathways 714 may be implemented by tubes and pumps, microfluidics, laboratory robotics, or other techniques known to those of ordinary skill in the art. The control circuitry 712 may also cause the synthesizer 706 to release the assembled oligonucleotides from the microelectrode array 102 when synthesis is complete.

Microfluidic technology facilitates the automation of chemical and biological protocols. These devices manipulate small quantities of liquid at smaller scales and with higher precision than humans. Digital microfluidic (DMF) technology is one type of flexible microfluidic technology. DMF devices manipulate individual droplets of liquids on a grid of electrodes, taking advantage of a phenomenon called electrowetting on dielectric. Activating electrodes in certain patterns can move, mix, or split droplets anywhere on the chip. Microfluidics also includes full-stack microfluidics which are programmable systems that allow unrestricted combination of computation and fluidics. Examples of microfluidic technology may be found in Willsey et al., *Puddle: A dynamic, error-correcting, full-stack microfluidics platform*, Aplos' 19, April 13-17, 183 (2019).

In an implementation, the synthesizer 706 may include multiple oligonucleotide complex pools 716. The oligonucleotide complexes may be pre-made using any oligonucleotide synthesis technique such as phosphoramidite synthesis and stored in the pools 716 where they are available to be transferred by fluid delivery pathways 714 to the reaction chamber 710. The oligonucleotide complexes may be stored in the pools 716 in an aqueous solution that uses a standard buffer for storing oligonucleotides. The concentration of oligonucleotide complexes in the pools 716 may be, for example, about 0.5, 1, 2, 3, 4, 5, 10, 15, 20, 30, or 50 nM.

There may be one or more pools 716 for each unique payload region encoded by the oligonucleotide complexes. For example, if the oligonucleotide complexes encode bits there will be one set of oligonucleotide complexes that encode "0" and another set of oligonucleotide complexes that include "1." In one implementation, each bit is represented by one of three different oligonucleotide complexes.

The bit "0" may be encoded by two complementary oligonucleotide complexes where one is an "alternative configuration" and that each contain the same payload sequence but with different and complementary sticky ends. These oligonucleotide complexes are represented as "0" a*/b and "0" a/b*. These may be the same as the oligonucleotide complexes 200 and 208 shown in FIG. 2.

Similarly, three different sets of oligonucleotide complexes may be used to encode "1." Thus, six different types of oligonucleotide complexes may be needed to encode two different arbitrary values. If the oligonucleotide complexes are used to encode more than two different arbitrary values such as encoding trits or letters of the English language then the number of oligonucleotide complex pools 716 will increase accordingly. Oligonucleotide complexes from each of the pools 716 may be moved into the reaction chamber 710 through a separate fluid delivery pathway 714(A), 714(B), 714(C), and 714(D).

One or more of a wash buffer 718, ligase 720, copper species 722, anchor/linkers 724, and other reagent(s) 726 may also be available in pools connected to the reaction chamber 710 by respective fluid delivery pathways 714(E), 714(F), 714(G), 714(H), and 714(I). The wash buffer 718 may include any wash buffer suitable for washing or manipulating oligonucleotides such as TE, TAE, and TBE. The wash buffer may be water, an aqueous buffer solution, or mixed aqueous/organic solvent. Examples of organic solvents that may be added to a wash buffer include polar, miscible organic cosolvents (e.g., DMSO, acetonitrile, etc.) which may be helpful in removing metal ions, organic residues, and denatured protein. The pool of ligase 720 may include DNA ligase and RNA ligase in appropriate buffer concentration for use in closing nicks in oligonucleotides within the reaction chamber 710.

The copper species 722 may be copper(I) that can be added to the reaction chamber 710 to activate the CuAAC reaction. In an implementation, the copper species 722 may be copper(II) which does not activate the CuAAC reaction. Following addition of copper(II) to the reaction chamber 710, it may be reduced at activated electrodes to copper(I) which then triggers the CuAAC reaction. Reduction may be performed globally across the entire surface of the microelectrode array 102 by activating all or substantially all of the electrodes 104. Alternatively, site-selective reduction may be performed by activating only some of the electrodes 104. This restricts the CuAAC reaction to only those electrodes 104 that are activated thereby controlling where formation of a triazole backbone occurs.

The anchors/linkers 724 may be used for preparing the microelectrode array 102 in the reaction chamber 710. This pool may include linkers 106 and/or anchor sequences 108. There may also be one or more additional pools or reservoirs that contain one or more other reagent(s) 726 such as an enzyme that cleaves the assembled oligonucleotide from the microelectrode array. The enzyme may recognize and cleave a nucleotide sequence found in the anchor sequences 108 that is not present in any of the assembled oligonucleotides. Also, the other reagents may include a chemical (e.g., ammonia) that cleaves a linker attaching the assembled oligonucleotide to the microelectrode array.

Illustrative Computer Architecture

Figure 8:
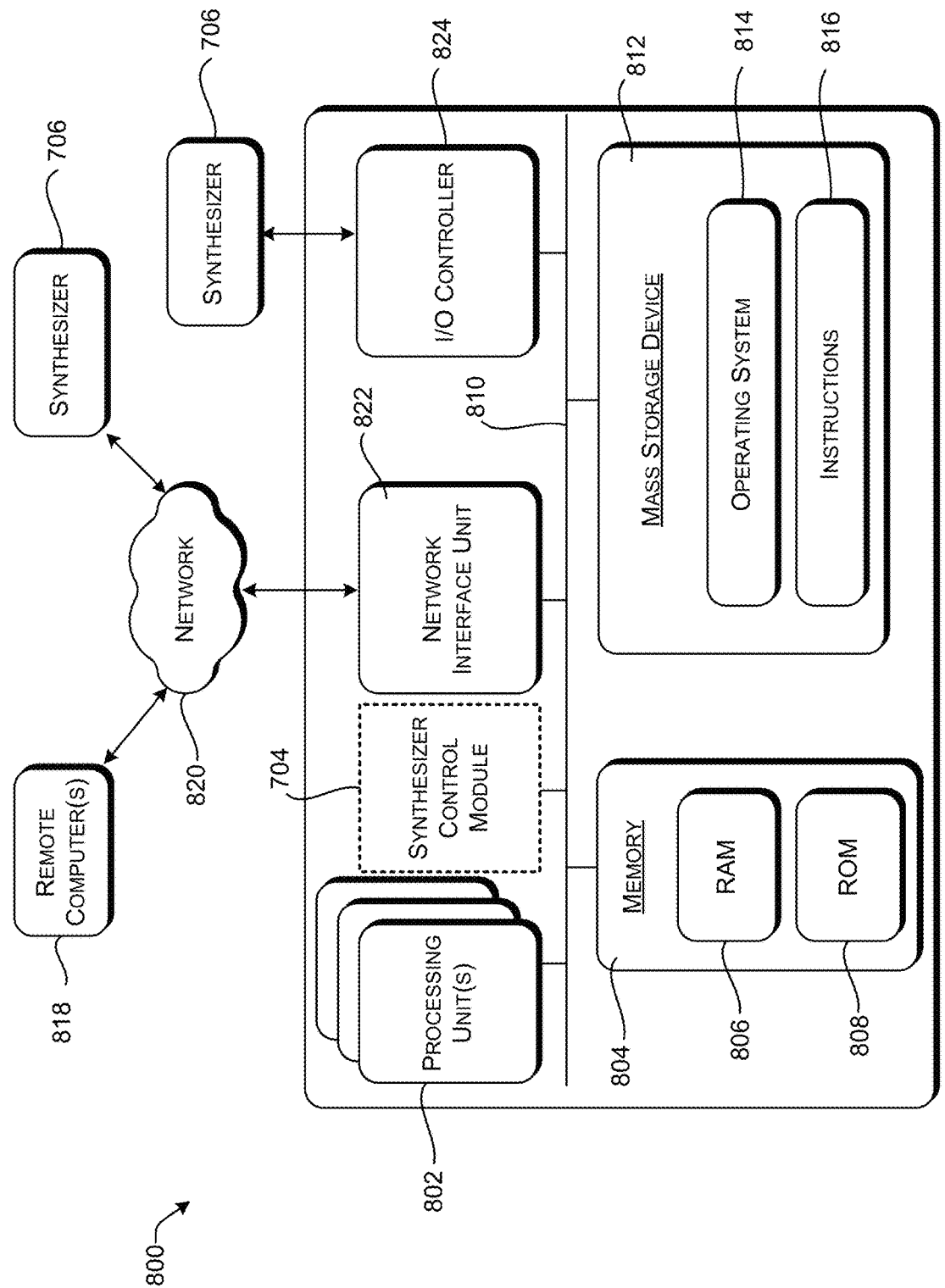
FIG. 8 is an illustrative computer architecture for implementing techniques of this disclosure.

FIG. 8 is a computer architecture diagram showing an illustrative computer hardware and software architecture for a computing device such as the computing device 702 introduced FIG. 7. In particular, the computer 800 illustrated in FIG. 8 can be utilized to implement the synthesizer control module 704.

The computer 800 includes one or more processing units 802, a system memory 804, including a random-access memory 806 ("RAM") and a read-only memory ("ROM") 808, and a system bus 810 that couples the memory 804 to the processing unit(s) 802. A basic input/output system ("BIOS" or "firmware") containing the basic routines that help to transfer information between elements within the computer 800, such as during startup, can be stored in the ROM 808. The computer 800 further includes a mass storage device 812 for storing an operating system 814 and other instructions 816 that represent application programs and/or other types of programs such as, for example, instructions to implement the synthesizer control module 704. The mass storage device 812 can also be configured to store files, documents, and data.

The mass storage device 812 is connected to the processing unit(s) 802 through a mass storage controller (not shown) connected to the bus 810. The mass storage device 812 and its associated computer-readable media provide non-volatile storage for the computer 800. Although the description of computer-readable media contained herein refers to a mass storage device, such as a hard disk, CD-ROM drive, DVD-ROM drive, or USB storage key, it should be appreciated by those skilled in the art that computer-readable media can be any available computer-readable storage media or communication media that can be accessed by the computer 800.

Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner so as to encode information in the signal. By way of example, and not limitation, communication media includes wired media such as a wired network or direct-wired connection, and wireless media such as acoustic, radio frequency, infrared, and other wireless media. Combinations of any of the above should also be included within the scope of computer-readable media.

By way of example, and not limitation, computer-readable storage media can include volatile and non-volatile, removable and non-removable media implemented in any method or technology for storage of information such as computer-readable instructions, data structures, program modules, or other data. For example, computer-readable storage media includes, but is not limited to, RAM 806, ROM 808, EPROM, EEPROM, flash memory or other solid-state memory technology, CD-ROM, digital versatile disks ("DVD"), HD-DVD, BLU-RAY™, 4K Ultra BLU-RAY™, or other optical storage, magnetic cassettes, magnetic tape, magnetic disk storage or other magnetic storage devices, or any other medium that can be used to store the desired information and which can be accessed by the computer 800. For purposes of the claims, the phrase "computer-readable storage medium," and variations thereof, does not include waves or signals per se or communication media.

According to various configurations, the computer 800 can operate in a networked environment using logical connections to a remote computer(s) 818 through a network 820. The computer 800 can connect to the network 820 through a network interface unit 822 connected to the bus 810. It should be appreciated that the network interface unit 822 can also be utilized to connect to other types of networks and remote computer systems. The computer 800 can also include an input/output controller 824 for receiving and processing input from a number of other devices, including a keyboard, mouse, touch input, an electronic stylus (not shown), or equipment such as a synthesizer 706 for synthesizing oligonucleotides. Similarly, the input/output controller 824 can provide output to a display screen or other type of output device (not shown).

It should be appreciated that the software components described herein, when loaded into the processing unit(s) 802 and executed, can transform the processing unit(s) 802 and the overall computer 800 from a general-purpose computing device into a special-purpose computing device customized to facilitate the functionality presented herein. The processing unit(s) 802 can be constructed from any number of transistors or other discrete circuit elements, which can individually or collectively assume any number of states. More specifically, the processing unit(s) 802 can operate as a finite-state machine, in response to executable instructions contained within the software modules disclosed herein. These computer-executable instructions can transform the processing unit(s) 802 by specifying how the processing unit(s) 802 transitions between states, thereby transforming the transistors or other discrete hardware elements constituting the processing unit(s) 802.

Encoding the software modules presented herein can also transform the physical structure of the computer-readable media presented herein. The specific transformation of physical structure depends on various factors, in different implementations of this description. Examples of such factors include, but are not limited to, the technology used to implement the computer-readable media, whether the computer-readable media is characterized as primary or secondary storage, and the like. For example, if the computer-readable media is implemented as semiconductor-based memory, the software disclosed herein can be encoded on the computer-readable media by transforming the physical state of the semiconductor memory. For instance, the software can transform the state of transistors, capacitors, or other discrete circuit elements constituting the semiconductor memory. The software can also transform the physical state of such components to store data thereupon.

As another example, the computer-readable media disclosed herein can be implemented using magnetic or optical technology. In such implementations, the software presented herein can transform the physical state of magnetic or optical media, when the software is encoded therein. These transformations can include altering the magnetic characteristics of particular locations within given magnetic media. These transformations can also include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer 800 to store and execute the software components presented herein. It also should be appreciated that the architecture shown in FIG. 8 for the computer 800, or a similar architecture, can be utilized to implement many types of computing devices such as desktop computers, notebook computers, servers, supercomputers, gaming devices, tablet computers, and other types of computing devices known to those skilled in the art. For example, the computer 800 may be wholly or partially integrated into the synthesizer 706. It is also contemplated that the computer 800 might not include all of the components shown in FIG. 8, can include other components that are not explicitly shown in FIG. 8, or can utilize an architecture completely different than that shown in FIG. 8.

EXAMPLES

Figure 9:
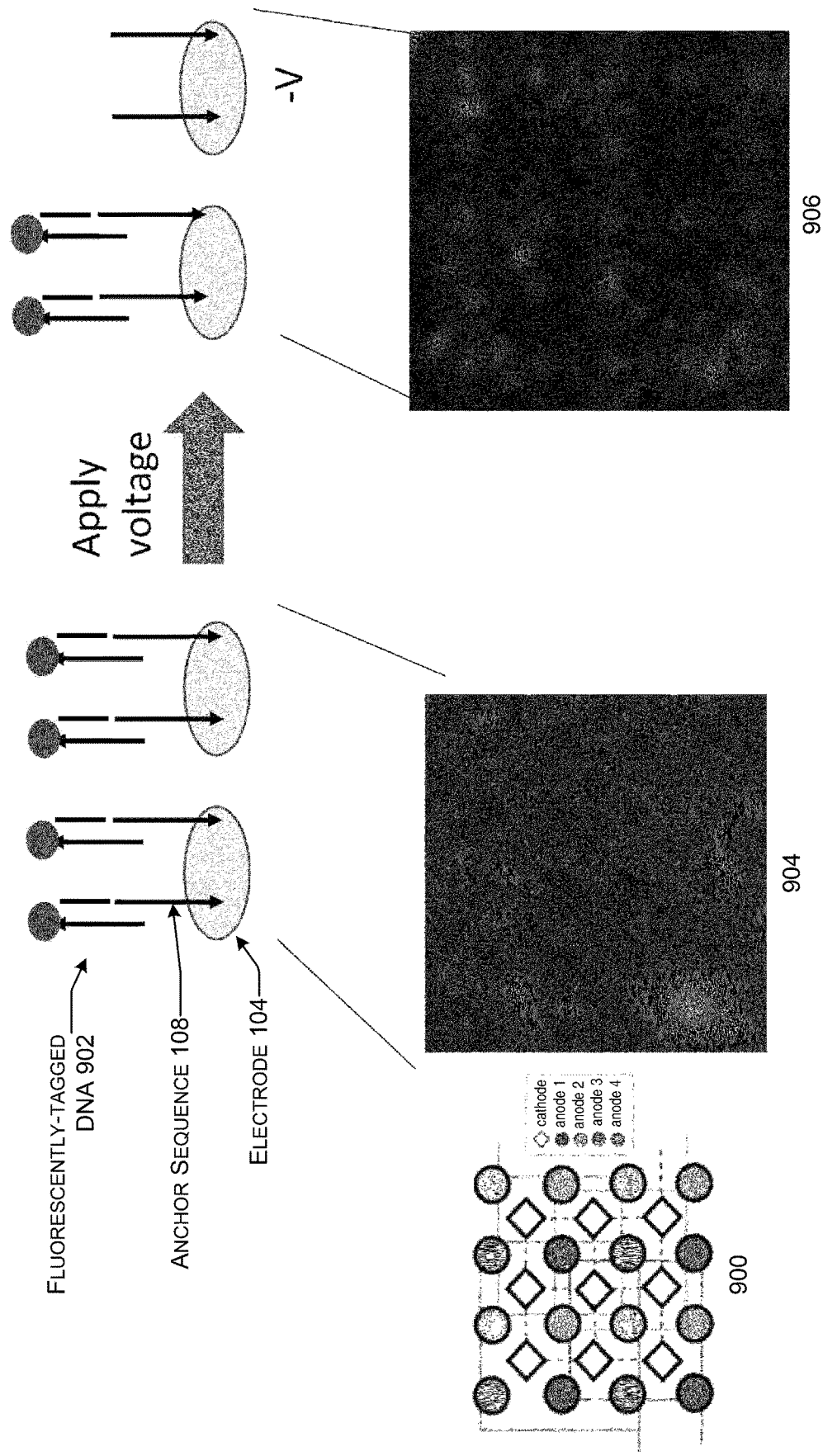
FIG. 9 is two fluorescent microscopy images showing loss of fluorescence due to de-hybridization of double-stranded DNA structures caused by generation of negative voltage at electrodes in a microelectrode array.

FIG. 9 shows a technique for selectively de-hybridization of double-stranded DNA by changing the voltage generated by a microelectrode array. To make the microelectrode array, a silicon wafer containing an array of 650 nm diameter electrodes pitched 2 μm was manufactured using standard nanolithography process technology. The wafer was diced and mounted on a FR4 PCB. The A and B face of the PCB were mirrored and designed for a high-density card interface. The die pins were wire bonded to their corresponding traces on the PCB and then protected by an epoxy encapsulate to create the slide assembly. To address the electrodes on the array, a card edge connector was connected to the slide assembly driven by a National Instruments PXIe-4141 Source Measure Unit. This design of a microelectrode array may be referred to as a passive chip.

The electrode configuration 900 on the surface of the microelectrode array has four sets of separately addressable anodes arranged in a repeating pattern. Circles represent the anodes; diamonds represent the cathodes. Cathodes are connected together (represented by the dashed line) while only anodes of the same color are connected together to generate four addressable electrodes (represented by the similarly-colored jumpers—solid lines). Although there are only four addressable electrodes 104 in this example, in other configurations each individual anode may be separately addressable.

To prepare the microelectrode array for synthesis, the surface was rinsed with DI water, treated with Nano-strip® for 90 seconds, rinsed with DI water, blown dry with compressed air, and stored in an oven at 90° C. until use.

To create anchor sequences 108, phosphoramidite reagents were diluted to 0.07 M with acetonitrile and loaded onto an Expedite™ 8900 oligonucleotide synthesizer following standard protocols. The microelectrode array was connected to the Expedite 8900, and the anchor sequences 108 were synthesized using the default fluidics protocols for column synthesis on 50 nmol scale. The surface-bound strands were deprotected by incubation in 30% ammonium hydroxide for 1 hour. The microelectrode array was washed with DI water and blown dry with compressed air.

A fluorescently tagged dsDNA complex 902 containing a sticky end complementary to the surface-bound anchor sequence 108 was hybridized by dissolving the components in 1× TAE buffer/12.5 mM $MgCl_2$ at a concentration of 10 heating to 95° C. for 1 min, then allowing the solution to cool to room temperature. The fluorescent tag was Texas Red. The complex was diluted to 1 μM with 5×TAE buffer/125 mM $MgCl_2$, and the microelectrode array prepared as described above was incubated in the resulting solution for 30 min. At the end of the incubation, the array was washed with DI water, 1 mg/mL SDS, and DI water, then blown dry with compressed air, and imaged at 100× with a fluorescence microscope.

Figure 10A:
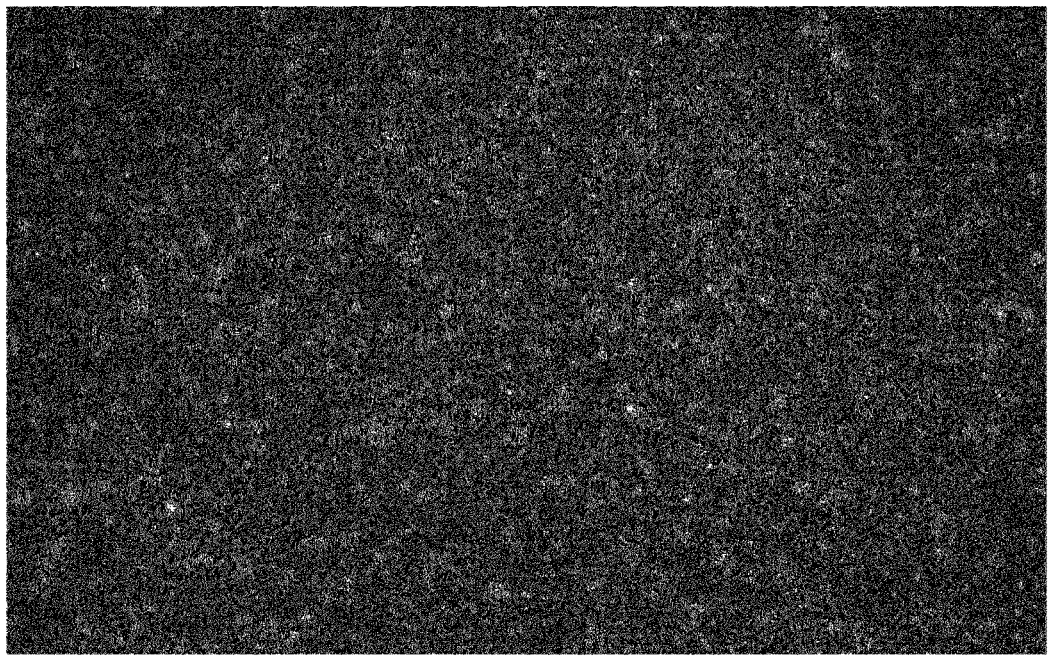
FIGS. 10A-B are the two fluorescent microscopy images from FIG. 9 showing a larger area of the microelectrode array.

The image 904 of a portion the microelectrode array prior to activation of electrodes 104 shows a pattern of fluorescence across the entirety of the microelectrode array surface resulting from hybridization of the fluorescently tagged dsDNA complexes 902 to the anchor sequences 108. It is believed that bright spots are attributable to noise resulting from inconsistencies in the surface chemistry. FIG. 10A is a fluorescent microscope image at 20X that shows a larger area of the microelectrode array surface than in the image 904 in FIG. 9. Fluorescence is apparent across the entire surface with hot spots due to noise.

Figure 10B:
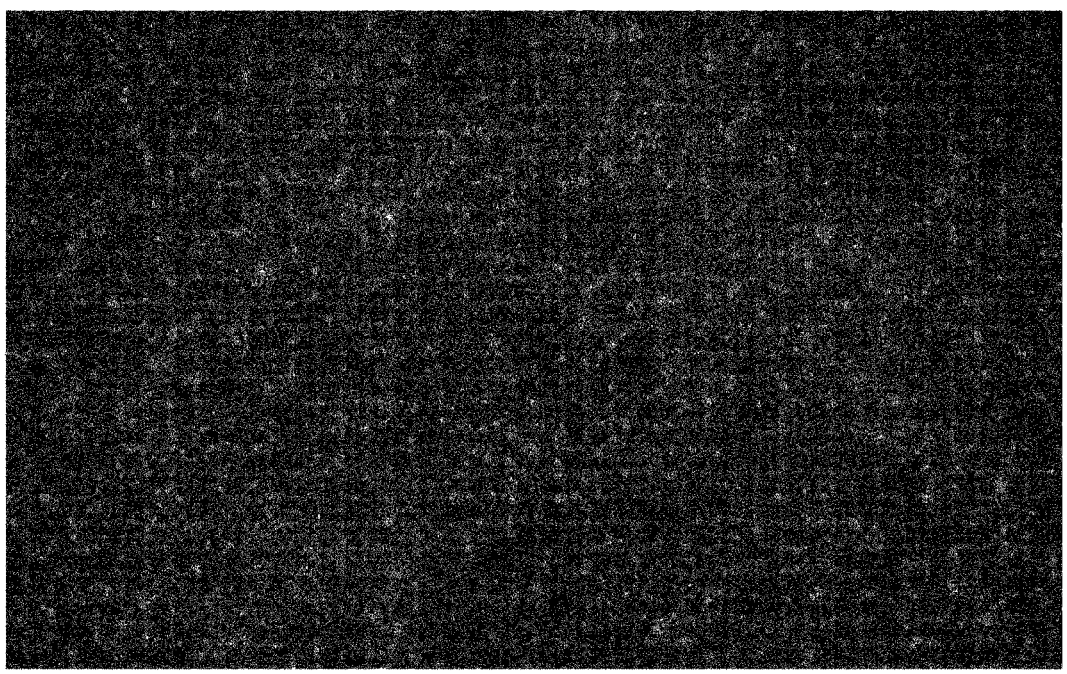

Voltage was applied leading to de-hybridization of the fluorescently tagged dsDNA complexes 902 at the activated anode. The microelectrode array was incubated in 50 mM potassium phosphate buffer, pH 7.4, and a potential of −1.6 V was applied for 90 seconds to one of the four addressable anodes. The array was washed with DI water, blown dry with compressed air, and imaged at 100× with a fluorescence microscope. The resulting image 906 shows an overall decrease in fluorescence and a pattern of dark spots correlating with the repeating pattern of the single activated electrode. Without being bound by theory, it is believed that the drop in background fluorescence is due to non-hybridized DNA being forced away from the surface due to electrostatic repulsion from negatively-charged electrodes. FIG. 10B is a fluorescent microscope image at 20× that shows a larger area of the microelectrode array when the electrodes 104 are generating a negative voltage. The emergence of a checkerboard pattern indicates a regular pattern of de-hybridization and disassociation from anchor sequences 108 as expected when activating one of the four anodes.

ILLUSTRATIVE EMBODIMENTS

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method of selectively assembling an oligonucleotide on a microelectrode array (102) coated with a plurality of anchor sequences (108), the method comprising: introducing a first oligonucleotide complex (110) encoding a first arbitrary value into a reaction chamber (710) containing the microelectrode array (102); activating a first subset of electrodes (104) in the microelectrode array (102) to attract the first oligonucleotide complex (110) to the first subset of electrodes (104) having attached thereto a first subset of anchor sequences (108); introducing a second oligonucleotide complex (118) encoding a second arbitrary value into the reaction chamber (710); activating a second subset of electrodes (104) in the microelectrode array (102) to attract the second oligonucleotide complex (110) to the second subset of electrodes (104) having attached thereto a second subset of anchor sequences (108); and closing nicks in assembled double-stranded oligonucleotides (402) attached to the microelectrode array (102), the assembled double-stranded oligonucleotides (402) formed at least in part by hybridization of the first oligonucleotide complex (110) to the first subset of anchor sequences (108) or by hybridization of the second oligonucleotide complex (118) to the second subset of anchor sequences (108).

Clause 2. The method of clause 1, wherein the first arbitrary value represents a first binary digit and the second arbitrary value represents a second binary digit.

Clause 3. The method of any of clauses 1-2, wherein closing the nicks comprises introducing a ligase into the reaction chamber.

Clause 4. The method of any of clauses 1-2, wherein an end of the first oligonucleotide complex is an azide and an end of the second oligonucleotide complex is an alkyne; and wherein, closing the nicks comprises initiating Cu(I)-catalyzed azide-alkyne cycloaddition (CuAAC).

Clause 5. The method of any of clauses 1-4, further comprising separating the assembled double-stranded oligonucleotides from the microelectrode array.

Clause 6. The method of any of clauses 1-5, wherein a sticky end of the first oligonucleotides complex has a sequence that hybridizes to any of the plurality of anchor sequences.

Clause 7. The method of any of clauses 1-6, further comprising: introducing a third oligonucleotide complex into the reaction chamber containing the microelectrode array, the third oligonucleotide complex having alternate sticky ends, wherein the third oligonucleotide complex is an alternate configuration of the first oligonucleotide complex or of the second oligonucleotide complex; and activating a third subset of electrodes in the microelectrode array to attract the third oligonucleotide complex to the third subset of electrodes, wherein the alternate sticky ends of the third oligonucleotide complex hybridize with sticky ends of the first oligonucleotide complex or with sticky ends of the second oligonucleotide complex.

Clause 8. A system for selectively assembling an oligonucleotide, the system (700) comprising: a microelectrode array (102) coated with a plurality of anchor sequences (108); a reaction chamber (710) in contact with the microelectrode array (102); a first fluid delivery pathway (714A-F) configured to introduce a first oligonucleotide complex (110) encoding a first arbitrary value into the reaction chamber (710); a second fluid delivery pathway (714A-F) configured to introduce a second oligonucleotide complex (112) encoding a second arbitrary value into the reaction chamber (710); and control circuitry (712) configured to selectively activate individual electrodes (104) in the microelectrode array (102), selectively open the first fluid delivery pathway (714A-F), and selectively open the second fluid delivery pathway (714A-F) in response to instructions (708) indicating a sequence of an assembled double-stranded oligonucleotide (402).

Clause 9. The system of clause 8, further comprising: a third fluid delivery pathway configured to deliver an alternate configuration of the first oligonucleotide complex having alternate sticky ends; and a fourth fluid delivery pathway configured to deliver an alternate configuration of the second oligonucleotide complex having alternate sticky ends.

Clause 10. The system of any of clauses 8-9, further comprising a third fluid delivery pathway configured to introduce a ligase into the reaction chamber.

Clause 11. The system of any of clauses 8-9, further comprising a third fluid delivery pathway configured to introduce a copper species into the reaction chamber.

Clause 12. The system of any of clauses 8-11, wherein the control circuitry is configured to, in response to instructions indicating completion of synthesis, introduce an enzyme that cleaves the assembled double-stranded oligonucleotide from the microelectrode array or introduce a chemical that cleaves a linker attaching the assembled double-stranded oligonucleotide to the microelectrode array.

Clause 13. The system of any of clauses 8-12, wherein the sequence of the assembled double-stranded oligonucleotide is provided in the instructions to the control circuitry as an ordered sequence of values including the first arbitrary value and the second arbitrary value.

Clause 14. The system of any of clauses 8-13, further comprising a fourth fluid delivery pathway configured to introduce the anchor sequences into the reaction chamber under conditions that cause the anchor sequences to coat the microelectrode array.

Clause 15. A method of encoding data by selectively assembling an oligonucleotide, the method comprising: attaching a plurality of anchor sequences (108) to a surface of a microelectrode array (102); hybridizing first initiating oligonucleotide complexes (214) encoding a first arbitrary value with a subset of the plurality of anchor sequences (108) attached to a subset of electrodes (104) in the microelectrode array (102) by activating the subset of electrodes (104) and introducing the first initiating oligonucleotide complexes (214) into a solution contacting the surface of the microelectrode array (102); hybridizing second oligonucleotide complexes (118) encoding a second arbitrary value with the first initiating oligonucleotide complexes (214) by activating the subset of electrodes (104) and introducing the second oligonucleotide complexes (118) into the solution contacting the surface of the microelectrode array (102); hybridizing alternate configurations of the second oligonucleotide complexes (118) encoding the second arbitrary value with the second oligonucleotide complexes (118) by activating the subset of electrodes (104) and introducing the alternate configurations of the second oligonucleotide complexes (118) into the solution contacting the surface of the microelectrode array (102); closing nicks in assembled double-stranded oligonucleotides (402) formed from the hybridizing of the anchor sequences (108), the first initiating oligonucleotide complexes (214), the second oligonucleotides complexes (118), and the alternate configurations of the second oligonucleotides complexes (118); and separating the assembled double-stranded oligonucleotides (402) from the surface of the microelectrode array (102).

Clause 16. The method of clause 15, wherein the first initiating oligonucleotide complexes are partially double-stranded oligonucleotides comprising a long sticky end that hybridizes to at least a portion of the anchor sequences and a second sticky end that hybridizes to other oligonucleotide complexes.

Clause 17. The method of clause 16, wherein the second oligonucleotide complexes are partially double-stranded oligonucleotides comprising a first sticky end that hybridizes to the second sticky end of the first initiating oligonucleotide complexes and a second sticky end that hybridizes to other oligonucleotide complexes.

Clause 18. The method of clause 17, wherein the alternate configurations of the second oligonucleotide complexes are partially double-stranded oligonucleotides comprising a first sticky end that hybridizes to the second sticky end of the second oligonucleotide complexes and a second sticky end that hybridizes to the first sticky end of the second oligonucleotide complexes.

Clause 19. The method of any of clauses 15-18, further comprising hybridizing first oligonucleotide complexes (110) encoding the first arbitrary value with the alternate configurations of the second oligonucleotide complexes (112B) by activating a subset of electrodes (104) introducing the first oligonucleotide complexes (110) into the solution contacting the surface of the microelectrode array (102).

Clause 20. The method of any of clauses 15-18, further comprising decoding the data by sequencing one or both strands of the assembled double-stranded oligonucleotides.

Clause 21. A method of selectively assembling oligonucleotides on a microelectrode array (102) coated with a plurality of anchor sequences (108), the method comprising: introducing multiple copies of a first oligonucleotide complex (110) having two sticky ends (204, 206) and encoding a first arbitrary value into a reaction chamber (710) containing the microelectrode array (102); incubating the first oligonucleotide complex (110) with the microelectrode array (102) so that the first oligonucleotide complex (110) hybridizes to the anchor sequences (108); inhibiting hybridization of the first oligonucleotide complex through changing local pH (114) by activating a first subset of electrodes on the microelectrode array (102); and closing nicks in the assembled oligonucleotides (116, 402) that remain hybridized to the anchor sequences (108).

Clause 22. The method of clause 21, wherein the first arbitrary value represents a binary digit.

Clause 23. The method of clause 21 or 22, wherein closing the nicks comprises introducing a ligase into the reaction chamber.

Clause 24. The method of clause 21 or 22, wherein an end of the first oligonucleotide complex is an azide and an end of a second oligonucleotide complex is an alkyne; and wherein, closing nicks comprises initiating Cu(I)-catalyzed azide-alkyne cycloaddition (CuAAC).

Clause 25. The method of any of clauses 21-24, wherein the negative voltage is between about −1 V and −3 V.

Clause 26. The method of any of clauses 21-24, wherein the anchor sequences comprise an i-motif sequence and activating the first subset of electrodes comprises generating a positive voltage sufficient to create a localized acid environment that causes the i-motif the local pH.

Clause 27. The method of any of clauses 21-26, further comprising separating the assembled oligonucleotides from the microelectrode array.

Clause 28. The method of any of clauses 21-25 or 27, wherein changing the local pH by activating the first subset of electrodes comprises creating a localized basic environment by activating the first subset of electrodes with a negative voltage sufficient to increase the pH such that double-stranded oligonucleotides de-hybridize.

Clause 29. The method of clause 28, further comprising: introducing multiple copies of a second oligonucleotide complex having two sticky ends and encoding a second arbitrary value into the reaction chamber containing the microelectrode array; incubating the second oligonucleotide complex with the microelectrode array so that the second oligonucleotide complex hybridizes to a free sticky end of the first oligonucleotide complex or the anchor sequences; creating a localized basic environment by activating a second subset of electrodes on the microelectrode array with the negative voltage sufficient to increase the pH such that double-stranded oligonucleotides de-hybridize; and closing nicks in the oligonucleotides anchored to the microelectrode array.

Clause 30. A system for selectively assembling an oligonucleotide, the system comprising: a microelectrode array (102) coated with a plurality of anchor sequences (108); a reaction chamber (710) in contact with the microelectrode array (102); a first fluid delivery pathway (714) configured to introduce a first oligonucleotide complex (110) encoding a first arbitrary value into the reaction chamber (710); a second fluid delivery pathway (714) configured to introduce a second oligonucleotide complex (118) encoding a second arbitrary value into the reaction chamber (710); and control circuitry (712) configured to selectively generate negative voltages sufficient to increase the pH such that double-stranded oligonucleotides de-hybridize in proximity to individual electrodes (104) in the microelectrode array (102), selectively open the first fluid delivery pathway (714), and selectively open the second fluid delivery pathway (714) in response to instructions indicating a sequence of an assembled oligonucleotide (116, 402), wherein oligonucleotide complexes do not hybridize in proximity to the individual electrodes (104) where the negative voltages are generated.

Clause 31. The system of clause 30, further comprising: a third fluid delivery pathway configured to deliver an alternate configuration of the first oligonucleotide complex having alternate sticky ends; and a fourth fluid delivery pathway configured to deliver an alternate configuration of the second oligonucleotide complex having alternate sticky ends.

Clause 32. The system of clause 30, further comprising a third fluid delivery pathway configured to introduce a ligase into the reaction chamber.

Clause 33. The system of any of clauses 30-32, wherein the control circuitry is configured to, in response to instructions indicating completion of synthesis, introduce an enzyme that cleaves the assembled oligonucleotide from the microelectrode array or introduce a chemical that cleaves a linker attaching the assembled oligonucleotide to the microelectrode array.

Clause 34. The system of any of clauses 30-33, wherein the sequence of the assembled oligonucleotide is provided in the instructions to the control circuitry as an ordered sequence of values including the first arbitrary value and the second arbitrary value.

Clause 35. A method of encoding data by selectively assembling an oligonucleotide, the method comprising: hybridizing first oligonucleotide complexes (110) encoding a first arbitrary value with a subset of a plurality of anchor sequences (108) attached to a subset of electrodes (104) in a microelectrode array (102) by (i) introducing the first oligonucleotide complexes (110) into a buffer contacting the surface of the microelectrode array (102) and (ii) generating a negative voltage that raises local pH of the buffer at electrodes (104) other than the subset of electrodes sufficiently to cause de-hybridization of double-stranded oligonucleotides; closing nicks in assembled oligonucleotides (116, 402) formed from the hybridizing of the first oligonucleotide complexes (110) and the anchor sequences (108); and separating the assembled oligonucleotides (116, 402) from the surface of the microelectrode array (402).

Clause 36. The method of clause 35, wherein attaching the plurality of anchor sequences comprises phosphoramidite synthesis of the anchor sequences on the surface of the microelectrode array.

Clause 37. The method of clause 35 or 36, wherein the buffer has an ionic strength of about 0.05M and the local pH is raised to about 10.

Clause 38. The method of any of clauses 35-37, wherein the first oligonucleotide complexes comprise a first sticky end that hybridizes to the anchor sequences and a second sticky end that hybridizes to a sticky end of second oligonucleotide complexes.

Clause 39. The method of any of clauses 35-38, wherein generating the negative voltage comprises generating a voltage of between about −1 V to −3 V for about 60 seconds to about 120 seconds.

Clause 40. The method of any of clauses 35-39, further comprising decoding the data by sequencing the assembled oligonucleotides.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

For ease of understanding, the processes discussed in this disclosure are delineated as separate operations represented as independent blocks. However, these separately delineated operations should not be construed as necessarily order dependent in their performance. The order in which the processes are described is not intended to be construed as a limitation, and unless other otherwise contradicted by context any number of the described process blocks may be combined in any order to implement the process or an alternate process. Moreover, it is also possible that one or more of the provided operations is modified or omitted.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications throughout this specification. Each of the cited references is individually incorporated herein by reference for its particular cited teachings as well as for all that it discloses.

The invention claimed is:

1. A method of selectively assembling oligonucleotides on a microelectrode array coated with a plurality of anchor sequences, the method comprising:
   introducing multiple copies of a first oligonucleotide complex having two sticky ends and encoding a first arbitrary value into a solution in a reaction chamber containing the microelectrode array;

incubating the multiple copies of the first oligonucleotide complex with the microelectrode array so that the multiple copies of the first oligonucleotide complex hybridize to the anchor sequences;

inhibiting hybridization of a first subset of the multiple copies of the first oligonucleotide complex through changing local pH by activating a first subset of electrodes on the microelectrode array such that double-stranded oligonucleotides de-hybridize at the first subset of electrodes but not at other locations on the surface of the microelectrode array; and closing nicks between ones of the multiple copies of the first oligonucleotide complex that remain hybridized to the anchor sequences thereby forming assembled oligonucleotides.

2. The method of claim 1, wherein the first arbitrary value represents only a single binary digit.

3. The method of claim 2, wherein an order of the binary digit and other binary digits encoded in the assembled oligonucleotides encodes data.

4. The method of claim 1, wherein closing the nicks comprises introducing a ligase into the reaction chamber.

5. The method of claim 1, further comprising introducing multiple copies of a second oligonucleotide complex to the reaction chamber containing the microelectrode array, wherein an end of individual ones of the multiple copies of the first oligonucleotide complex is an azide and an end individual ones of the multiple copies of the second oligonucleotide complex is an alkyne; and wherein, closing nicks comprises initiating Cu(I)-catalyzed azide-alkyne cycloaddition (CuAAC).

6. The method of claim 1, wherein a voltage generated by the first subset of electrodes is a negative voltage that is between about −1 V and −3 V.

7. The method of claim 1, wherein the anchor sequences comprise an i-motif sequence and activating the first subset of electrodes comprises generating a positive voltage sufficient to create a localized acid environment that causes the i-motif sequence to adopt a folded confirmation.

8. The method of claim 1, further comprising separating the assembled oligonucleotides from the microelectrode array.

9. The method of claim 1, wherein changing the local pH by activating the first subset of electrodes comprises creating a localized basic environment by activating the first subset of electrodes with a negative voltage sufficient to increase the pH such that double-stranded oligonucleotides de-hybridize.

10. The method of claim 9, further comprising:

introducing multiple copies of a second oligonucleotide complex having two sticky ends and encoding a second arbitrary value into the reaction chamber containing the microelectrode array;

incubating the multiple copies of the second oligonucleotide complex with the microelectrode array so that individual ones of the multiple copies of the second oligonucleotide complex hybridize to a free sticky end of an individual one of the multiple copies of the first oligonucleotide complex or a one of the anchor sequences;

creating a localized basic environment by activating a second subset of electrodes on the microelectrode array with the negative voltage sufficient to increase the pH such that double-stranded oligonucleotides de-hybridize at the second subset of electrodes but not at other locations on the surface of the microelectrode array; and closing nicks between the individual ones of the multiple copies of the second oligonucleotide complex that remain hybridized to ones of the multiple copies of the first oligonucleotide complex or the anchor sequences thereby anchoring the individual ones of the multiple copies of the second oligonucleotide complex to the microelectrode array.

11. The method of claim 1, further comprising attaching the anchor sequences to the microelectrode array by phosphoramidite synthesis of the anchor sequences on the surface of the microelectrode array.

12. The method of claim 1, wherein the multiple copies of the first oligonucleotide complex comprises a first sticky end that hybridizes to the anchor sequences and a second sticky end that hybridizes to a sticky end of a second oligonucleotide complex.

13. The method of claim 1, wherein during the incubating all or substantially all of the plurality of anchor sequences hybridize to individual ones of the multiple copies of the first oligonucleotide complex.

14. A method of encoding data by selectively assembling oligonucleotide complexes encoding arbitrary values into oligonucleotides, the method comprising:

hybridizing first oligonucleotide complexes encoding a first arbitrary value with a subset of a plurality of anchor sequences attached to a subset of electrodes in a microelectrode array by (i) introducing the first oligonucleotide complexes into a buffer contacting the surface of the microelectrode array and (ii) generating a negative voltage that raises local pH of the buffer at electrodes other than the subset of electrodes sufficiently to cause de-hybridization of double-stranded oligonucleotides at electrodes other than the subset of electrodes but not at the subset of electrodes;

closing nicks in assembled oligonucleotides formed from the hybridizing of the first oligonucleotide complexes and the plurality of anchor sequences attached to the subset of electrodes; and separating the assembled oligonucleotides from the surface of the microelectrode array.

15. The method of claim 14, wherein attaching the plurality of anchor sequences comprises phosphoramidite synthesis of the plurality of anchor sequences on the surface of the microelectrode array.

16. The method of claim 14, wherein the first oligonucleotide complexes comprise a first sticky end that hybridizes to the anchor sequences and a second sticky end that hybridizes to a sticky end of second oligonucleotide complexes.

17. The method of claim 14, wherein generating the negative voltage at the electrodes other than the subset of electrodes comprises generating a voltage of between about −1 V to −3 V for about 60 seconds to about 120 seconds.

18. The method of claim 14, further comprising decoding the data by sequencing the assembled oligonucleotides.

19. The method of claim 14, wherein (i) introducing the first oligonucleotide complexes into the buffer contacting the surface of the microelectrode array is performed such that all or substantially all of the plurality of anchor sequences hybridize to individual ones of the first oligonucleotide complexes prior to (ii) generating the negative voltage at electrodes other than the subset of electrodes.

20. The method of claim 14, wherein (i) introducing the first oligonucleotide complexes and (ii) generating the negative voltage are performed substantially simultaneously so that the multiple copies of the first oligonucleotide are prevented from hybridizing with a subset of the plurality of the anchor sequences at the electrodes other than the subset of electrodes.

* * * * *